US007026136B2

(12) United States Patent
Oethinger et al.

(10) Patent No.: US 7,026,136 B2
(45) Date of Patent: *Apr. 11, 2006

(54) METHODS OF REDUCING MICROBIAL RESISTANCE TO DRUGS

(75) Inventors: Margaret Oethinger, Bad Oeynhausen (DE); Stuart B. Levy, Boston, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/629,340

(22) Filed: Jul. 28, 2003

(65) Prior Publication Data

US 2005/0261165 A1    Nov. 24, 2005

Related U.S. Application Data

(63) Continuation of application No. 09/966,835, filed on Sep. 28, 2001, now Pat. No. 6,677,133, which is a continuation of application No. 09/358,948, filed on Jul. 22, 1999, now Pat. No. 6,346,391.

(51) Int. Cl.
  *C12Q 1/18*  (2006.01)
  *C12Q 1/02*  (2006.01)
  *C12Q 1/00*  (2006.01)
  *C12Q 1/48*  (2006.01)

(52) U.S. Cl. .............................. 435/32; 435/29; 435/4; 435/15; 435/16; 435/23; 435/24

(58) Field of Classification Search ................... 435/32, 435/29, 4, 15, 16, 23, 24
See application file for complete search history.

(56) References Cited

U.S. PATENT DOCUMENTS

| 4,806,529 | A | 2/1989 | Levy | ........................... 514/154 |
| 5,021,407 | A | 6/1991 | Levy | ........................... 514/154 |
| 5,064,821 | A | 11/1991 | Levy | ........................... 514/154 |
| 5,179,096 | A | 1/1993 | Gentilini et al. | ............ 514/253 |
| 5,258,372 | A | 11/1993 | Levy | ........................... 514/154 |
| 5,589,470 | A | 12/1996 | Levy | ........................... 514/154 |
| 5,789,188 | A | 8/1998 | Rothstein et al. | ............. 435/29 |
| 5,811,412 | A | 9/1998 | Levy | ........................... 514/154 |
| 5,817,793 | A | 10/1998 | Levy | ........................ 536/24.1 |
| 5,989,832 | A | 11/1999 | Trias et al. | .................. 435/7.2 |

(Continued)

FOREIGN PATENT DOCUMENTS

WO    WO 96/33285    10/1996

(Continued)

OTHER PUBLICATIONS

Aono, Rikizo (1998) "Improvement of Organic Solvent Tolerance Level of *Escherichia Coli* by Overexpression of Stress-Responsive Genes", Extremophiles vol. 2 p. 239-248.

(Continued)

*Primary Examiner*—Louise N. Leary
(74) *Attorney, Agent, or Firm*—Lahive & Cockfield; Elizabeth A. Hanley; Megan E. Williams

(57) ABSTRACT

The instant methods and compositions represent an advance in controlling drug resistance in microbes. AcrAB-like efflux pumps have been found to control resistance to drugs, even in highly resistant microbes. Accordingly, methods of treating infection, methods of screening for inhibitors of AcrAB-like efflux pumps, and methods of enhancing antimicrobial activity of drugs are provided. Pharmaceutical composition comprising an inhibitor of an AcrAB-like efflux pump and an antimicrobial agent are also provided.

27 Claims, 1 Drawing Sheet

U.S. PATENT DOCUMENTS

| | | | | |
|---|---|---|---|---|
| 6,068,972 | A | 5/2000 | Levy | 435/4 |
| 6,326,391 | B1 | 12/2001 | Markham et al. | 514/410 |
| 6,346,391 | B1 * | 2/2002 | Oethinger et al. | 435/32 |
| 6,448,006 | B1 * | 9/2002 | Levy | 435/6 |
| 6,677,133 | B1 * | 1/2004 | Oethinger et al. | 435/32 |

FOREIGN PATENT DOCUMENTS

| | | |
|---|---|---|
| WO | WO 99/37667 | 1/1999 |
| WO | WO 99/17607 | 4/1999 |
| WO | WO 99/17760 | 4/1999 |
| WO | WO 99/17791 | 4/1999 |
| WO | WO 99/32657 | 7/1999 |
| WO | WO 99/37800 | 7/1999 |
| WO | WO 00/01714 | 1/2000 |
| WO | WO 00/32196 | 6/2000 |
| WO | WO 96/23075 | 8/2000 |

OTHER PUBLICATIONS

Brenwald, N.P. et al.Fluoroquinolone Resistance in *Streptococcus pneumoniae* by an Efflux Mechanism, Abstr of the 37th Inersc. Conference on Antimicrobial Agents and Chemotherapy.

Buysse, J.M. et al. (1996) "Mutation of the AcrAB antibiotic efflux pump in *Escherichai coli* confers susceptibility to oxazolidinone antibiotics" Abstracts of the Interscience Conference Of Antimicrobial Agents And Chemotherapy, vol. 36, No. 0, pp. 41. 36th ICAAC (International Conference of Antimicrobial Agents and Chemotherapy) New Orleans, Louisiana, USA. Sep. 15-18.

Cohen, Seth P. et al. (1989) "Cross-Resistance to Fluoroquinolones In Multiple-Antibiotic-Resistant (Mar) *Escherichia coli* Selected By Tetracycline Or Chloramphenicol: Decreased Drug Accumulatin Associated With Membrane Changes In Addition To OmpF Reduction" Antimicrobial Agents and Chemotherapy, vol. 33, No. 8, pp. 1318-1325.

Fourner, B. et al. A mutation in griB Gene of topoisomerase IV from *Staphlococcus aureus* Causes an Increase of Fluoroquinolone Resistance and A Decrease of coumarin Resistance, Abstracts of the 37th Interscience Conference on Antimicrobial Agents and Chemotherapy.

Goldman, John D. (1996) "Multiple Antibiotic Resistance (mar) Locus Protects *Escherichia coli* From Rapid Cell Killing by Fluoroquinolones" Antimicrobial Agents and Chemotherapy, vol. 40, No. 5, pp. 1266-1269.

Gustafson, John E. et al. (1999) "Growth In The Presence of Salicylate Increases Fluoroquinolone Resistance In Staphylococcus Aureus" Antimicrobial Agents and Chemotherapy, vol. 45, No. 4 pp. 990-992.

Hooper DC, et al. (1987) "Mechanisms of action of and resistance to ciprofloxacin". Am J Med. 82(4A).

Hullen, V. et al. (1998) "Induction of the mar Phenotype Is a Possible Cause for The Development of Fluoroquinolone Resistance In *Escherichia coli*," Antimicrob. Resist. Action.

Kern, W. V. et al. Selection of high-level fluoroquinolone-resistant *Echerichia coli* mutants in-vitro:involvement of the mar or Sox system, Abstracts of the 37th Inerscience Conference on Antimicrobial Agents and Chemotherapy.

Levy, Colin W et al. (1999) "Molecular Basis of Triclosan Activity" Nature, vol. 398, pp. 383-384.

Lewis, Kim (1996) "Multidrug Resistance Pumps Provide Broad Defense" ASM News, vol. 63, No. 11 pp. 605-610.

Lewis, Kim (1994) "Multidrug Resistance Pumps In Bacteria; Variations On a Theme"TIBS 19, pp. 119-123.

Lomovskaya, O. et al. "Identification and characterization of Efflux Pump Inhibitors in *P. aeruginosa*", Abstract No. F-1264, Poster Presentation at the 38th Inerscience Conference on Antimicrobial Agents and Chemotherapy.

Lomovskaya, O. et al. "Inhibitors of Efflux Pumps in *Pseudomonas aeuruginosa* Potentiate the Activity of the Fluroquinolone Antibacterial Levoflaxacin", Abstract No. F-1265, Poster Presentation at the 38th Inerscience Conference on Antimicrobial Agents and Chemotherapy.

Lomovskaya, O. et al. "Effux Pump Inhibitors (EPIs) Enhance the Activity of antrimicrobial Agents against a road Selection of Bacteria", Abstract No. F-1266, Poster Presentation at the 38th Inerscience Conference on Antimicrobial Agents and Chemotherapy.

Lomovskaya, O. et al. "Prevalence of Efflux Pump Overexpression Among Clinical Isolates of PseudomonEffux Pump Inhibitors (EPIs) Enhance the Activity of antrimicrobial Agents against a road Selection of Bacteria", Abstact No. F-1267, Poster Presentation at the 38th Inerscience Conference on Antimicrobial Agents and Chemotherapy.

Lomovskaya, O. et al. "Potentiation of Levoloxacin (levo) by a Broad-Spectrum Efflux Pump Inhibitor ('EPI) in Mouse Models of Infection Due to Pseudomanaaeurinasa", Abstact No. F-1268, Poster Presentation at the 38th Inerscience Conference on Antimicrobial Agents and Chemotherapy.

Lomovskaya, O. et al. "Inhibitors of Fungal Efflux Pump", Abstact No. F-1269, Poster Presentation at the 38th Inerscience Conference on Antimicrobial Agents and Chemotherapy.

Lomovskaya, Olga et al. (1999) "Use of a Genetic Approach To Evaluate the Consequences of Inhibition of Efflux Pumps in *Pseudomonas aeruginosa* " Antimicrobial Agents and Chemotherapy, vol. 43, No. 6, pp. 1340-1346.

Markham PN, et al. (1999)Multiple novel inhibitors of the NorA multidrug transporter of *Staphylococcus aureus*. *Antimicrob Agents Chemother.*;43(10):2404-8.

Ma, Dzwokai et al. (1995) "Genes acrA and acrB Encode A Stress-Induced Efflux System of *Escherichia Coli*" Molecular Microbiology vol. 16, No. 1, pp. 45-55.

Ma, Dzwoka et al. (1996) "The Local Repressor AcrR Plays A Modulating Role In The Regulation of acrAB Genes of *Escherichia coli*by Global Stress Signals" Molecular Microbiology, vol. 19, No. 1, pp. 101-112.

McMurry, Laura et al. (1998) Overexpression of marA, soxS, or acrAB produces resistance to triclosan in *Escherichia coli*: FEMS Microbiol. Lett. 166(2), 305-309.

McMurry, Laura et al. (1994) "Active Efflux of Chloramphenicol In Susceptible *Escherichia coli* Strains and in Multiple-Antibiotic-Resistant (Mar) Mutants" Antimicrobial Agents and Chemotherapy, vol. 38, No. 3, pp. 542-546.

Miller, Paul F and Sulavik, Mark C. (1996) "Overlaps and Paralels In The Regulation of Intrinsic Multiple-Antibiotic Resistance In *Escherichia coli*" Molecular Microbiology, vol. 21, No. 3, pp. 441-448.

Moken, Merri C. et al. (1997) "Selectin of Multiple-Antibiotic-Resistant (Mar) Mutants of *Escherichia coli* by Using the Disinfectant Pine Oil: Roles of the mar and acrAB Loci" Antimicrobial Agents and Chemotherapy vol. 41, No. 12, pp. 2770-2772.

Nikaido, Hiroshi (1996) "Multidrug Efflux Pumps of Gram-Neative Bacteria" Journal of Bacteriology vol. 178, No. 20 pp. 5853-5859.

Nikaido, Hiroshi et al. (1998) "Multidrug Efflux Pump AcrAB of *Salmonella typhimurium* Excretes Only Those β-Lactam Antibiotics Containing Lipophilic Side Chains" Journal of Bacteriology, vol. 180, No. 17, pp. 4686-4692.

Oethinger, M. et al., (1998) "Ineffectiveness of Topoisomerase Mutations in *Escherichia coli* in the Absence of the AcrAB Multidrug Efflux Pump" Preseented at the 38th Interscience Conference on Antimicrobial Agents and Chemotherapy; Sep. 24-27, 1998 in San Diego, CA. (Abstract No. C125).

Oethinger, Margret et al. (1998) "Overexpression of the marA or soxS Regulatory Gene in Clinical Topoisomerase Mutants of *Escherichia coli*" Antimicrobial Agents and Chemotherapy, vol. 42, No. 8 pp. 2089-2094.

Oethinger, Margret et al. (1998) "Associate of Organic Solvent Tolerance and Fluoroquinolone Resistance In Clinical Isolates of *Escherichia coli*" Journal of Antimicrobial Chemotherapy, vol. 41, pp. 111-114.

Okusu, Haruko et al. (1996) "AcrAB Efflux Pump Plays a Major Role in the Antibiotic Resistance Phenotype of *Escherichia coli* Multiple-Antibiotic-Resistance (Mar) Mutants" Journal of Bacteriology vol. 178, No. 1 pp. 306-308.

Park, Yoon-Hee et al. (1996) "Molecular Analysis of Fluoroquinolone-Resistance in *Escherichia coli* on the Aspect of Gyrase and Multiple Antibiotic Resistance (mar) Genes" Medical Journal, vol. 39, No. 4 pp. 514-540.

Paulsen, Ian T. et al. (1996) "Proton-Dependent Multidrug Efflux Systems" Microbiological Reviews vol. 60, No. 4 pp. 575-608.

Sanchez, Laura et al. (1997) The *acrAB* Homolog of *Haemophilus influenzae* Codes for a Functional Multidrug Efflux Pump, vol. 179(21), pp. 6855-6857.

Schmitz, Franz-Josef et al. (1998) "The Effect of Reserpine, An Inhibitor of Multidrug Efflux Pumps, On The In-Vitro Activities of Ciprofloxacin, Sparfloxacin and Moxifloxacin Against Clinical Isolates of *Staphylococcus aureus*" Journal of Antimicrobial Chemotherapy vol. 42, pp. 807-810.

Spratt, Brian G. (1994) "Resistance to Antibiotics Mediated by Target Alterations" Science vol. 264, pp. 388-392.

Sun, Li (1996) "NorA Plasmid Resistance to Fluoroquinolones: Roles of Copy Number and norA Frameshift Mutations" Antimiscrobial Agents and Chemotherapy vol. 40, No. 7, pp 1665-1669.

Tanaka, Toshihiko et al. (1997) "RobA-induced multiple antibiotic resistance largely depends on the activation of the AcrAB efflux" Microbiol. Immunol. 41(9), 697-702.

Tankovic J, et al. (1996) "Contributions of mutations in gyrA and parC genes to fluoroquinolone resistance of mutants of *Streptococcus pneumoniae* obtained in vivo and in vitro" Antimicrob Agents Chemother;40(11):2505-10.

White, David G. et al. (1997) "Role of the acrB Locus In Organic Solvent Tolerance Mediated By Expression of marA, soxS, or robA in *Escherichia coli*" Journal of Bacteriology vol. 179, No. 19 pp 6122-6126.

* cited by examiner

METHODS OF REDUCING MICROBIAL RESISTANCE TO DRUGS

GOVERNMENT FUNDING

This work was funded, at least in part, by a research grant from the U.S. Public Health Service GM 51661. The government, therefore, may have certain rights in the invention.

BACKGROUND OF THE INVENTION

Different drugs used to inhibit microbial growth act by inhibiting different targets. For example, the fluoroquinolone class of antibiotics act by inhibiting bacterial DNA synthesis. When used in treatment, fluoroquinolones are well absorbed orally, are found in respiratory secretions in higher concentrations than in serum and are concentrated inside macrophages. In addition, fluoroquinolones are well tolerated and have an excellent safety record in long-term therapy.

Antibiotic resistance, and in particular resistance to fluoroquinolones, has become a problem. Fluoroquinolone resistance in gram negative bacteria is principally caused by mutations affecting the target proteins of the drugs. In the case of fluoroquinolones, these targets are DNA gyrase and topoisomerase IV. In addition, mutations affecting regulatory genes such as marA, soxS or rob can cause fluoroquinolone resistance (Oethinger et al. 1998. *J. Antimicrob. Chemother.* 41:111). Mar A is a transcriptional activator encoded by the marRAB operon involved in multiple antibiotic resistance (Alekshun et al. (1997) *Antimicrob. Agents Chemother.* 41, 2067–2075). The marRAB locus confers resistance to tetracycline, chloramphenicol, fluoroquinolones, nalidixic acid, rifampin, penicillin, as well as other compounds. However, marRAB does not encode a multidrug efflux system. Rather, it controls the expression of other loci important in directly mediating drug resistance, e.g., ompF, the gene for outer membrane porin, and the acrAB genes for the AcrAB efflux proteins.

AcrAB is a multidrug efflux pump (Nikaido, H. (1996) *J. Bacteriol.* 178, 5853–5859; Okusu et al. (1996) *J. Bacteriol.* 178, 306–308) whose normal physiological role is unknown, although it may assist in protection of cells against bile salts in the mammalian small intestine (Thanassi et al. (1997) *J. Bacteriol.* 179, 2512–2518). The AcrAB operon is upregulated by MarA (Ma et al. (1995) *Mol. Microbiol.* 16, 45–55). Mutations in the repressor gene marR lead to overexpression of marA (Alekshun et al. (1997). *Antimicrob. Agents Chemother.* 41, 2067–2075; Cohen et al. (1993) *J. Bacteriol.* 175, 1484–492); Seoane et al. (1995) *J. Bacteriol.* 177, 3414–3419). The soxS gene encodes a MarA homolog (Alekshun et al. (1997) *Antimicrob. Agents Chemother.* 41, 2067–2075; Li et al. (1996) *Mol. Microbiol.* 20, 937–945; Miller et al. (1996) *Mol. Microbiol.* 21, 441–448) which also positively regulates acrAB (Ma et al. (1996) *Mol. Microbiol.* 19, 101–112).

The AcrAB pump primarily controls resistance to large, lipophilic agents that have difficulty penetrating porin channels, such as erythromycin, fusidic acid, dyes, and detergents, while leaving microbes susceptible to small antibiotics that can diffuse through the channel, e.g., tetracycline, chloramphenicol, and fluoroquinolones (Nikaido. 1996. *J. Bacteriology* 178:5853). Recently, the AcrAB pump has been found to be important in mediating resistance to other drugs used to control microbial growth, e.g., non-antibiotic agents such as triclosan (FEMS *Microbiol Lett* 1998 Sep. 15; 166: 305–9.

Microbes often become resistant to antibiotics and/or non-antibiotic agents. This can occur by the acquisition of genes encoding enzymes that inactivate the agents, modify the target of the agent, or result in active efflux of the agent. Enzymes that inactivate synthetic antibiotics such as quinolones, sulfonamides, and trimethoprim have not been found. In the case of these antibiotics and natural products for which inactivating or modifying enzymes have not emerged, resistance usually arises by target modifications (Spratt. 1994. *Science* 264:388). Improved methods for controlling drug resistance in microbes, in particular in microbes that are highly resistant to drugs, would be of tremendous benefit.

SUMMARY OF THE INVENTION

The present invention is based, at least in part, on the discovery that inactivation of the AcrAB locus makes even resistant microbial cells hypersusceptible to antibiotics and non-antibiotic drugs. Surprisingly, this is true even among highly resistant microbes which have chromosomal mutations that render them highly resistant to drugs.

Accordingly, in one aspect, the invention provides methods of treating an infection caused by a drug resistant microbe in a subject by administering a drug to which the microbe is resistant and an inhibitor of an AcrAB-like efflux pump to the subject such that the infection is treated.

In one embodiment, the drug is an antibiotic. In a preferred embodiment the antibiotic is selected from the group consisting of a fluoroquinolone and rifampin. In another embodiment, the drug is a non-antibiotic agent. In another embodiment, the drug is the non-antibiotic agent, triclosan.

In one embodiment, the inhibitor of an AcrAB-like efflux pump is administered prophylacticly. In another embodiment, the inhibitor of an AcrAB-like efflux pump is administered therapeutically.

In another aspect, the invention pertains to a method of treating a fluoroquinolone resistant infection in a subject comprising administering a fluoroquinolone and an inhibitor of an AcrAB-like efflux pump to the subject to thereby treat a fluoroquinolone resistant infection.

In another aspect, the invention pertains to a method of screening for compounds which reduce drug resistance comprising: contacting a microbe comprising an AcrAB-like efflux pump with a test compound and a indicator compound and measuring the effect of the test compound on efflux of the indicator compound to thereby identify compounds which reduce drug resistance by testing the ability of the test compound to inhibit the activity of an AcrAB efflux pump.

In one embodiment, the microbe is drug resistant. In a preferred embodiment, the microbial cell is highly drug resistant. In a more preferred embodiment, the microbe is highly resistant to fluoroquinolones. In another embodiment, the microbial cell comprises at least one mutation in a drug target gene. In another embodiment the microbial cell cmprises at least two mutations in a drug target gene. In a preferred embodiment, a mutation is present in a gene selected from the group consisting of: gyrase (gyrA), topoisomerase (parC), RNA polymerase, and fabI In one embodiment, the subject assay includes detecting the ability of the compound to reduce fluoroquinolone resistance in a microbe.

In another aspect, the invention provides a method of screening for compounds which specifically inhibit the activity of an AcrAB-like efflux pump comprising:

i) contacting a microbe comprising an AcrAB-like efflux pump with a test compound and an indicator compound;

ii) testing the ability of the compound to inhibit the activity of an AcrAB-like efflux pump;

iii) testing the ability of the compound to inhibit the activity of a non-AcrAB efflux pump;

iv) and identifying compounds which inhibit the activity of an AcrAB-like efflux pump and non a non-AcrAB-like efflux pump to thereby identify compounds which specifically block an AcrAB-like efflux pump.

In yet another aspect, the invention provides a method of enhancing the antimicrobial activity of a drug comprising: contacting a microbe that is highly resistant to one or more drugs with a drug to which the microbe is resistant and an inhibitor of an AcrAB-like efflux pump to thereby enhance the antimicrobial activity of a drug.

In one embodiment, the step of contacting occurs ex vivo. In one embodiment, the microbe is contacted with a non-antibiotic agent and an inhibitor of an AcrAB-like efflux pump. In one embodiment, the non-antibiotic agent is selected from the group consisting of: cyclohexadine, quaternary ammonium compounds, pine oil, triclosan, and compound generally regarded as safe (GRAS).

In another aspect, the invention provides a pharmaceutical composition comprising an inhibitor of an AcrAB-like efflux pump and an antibiotic. In one embodiment, the pharmaceutical composition further comprises a pharmaceutically acceptable carrier. In a preferred embodiment, the antibiotic is selected from the group consisting of fluoroquinolone and rifampin.

DETAILED DESCRIPTION OF THE INVENTION

Figure 1:
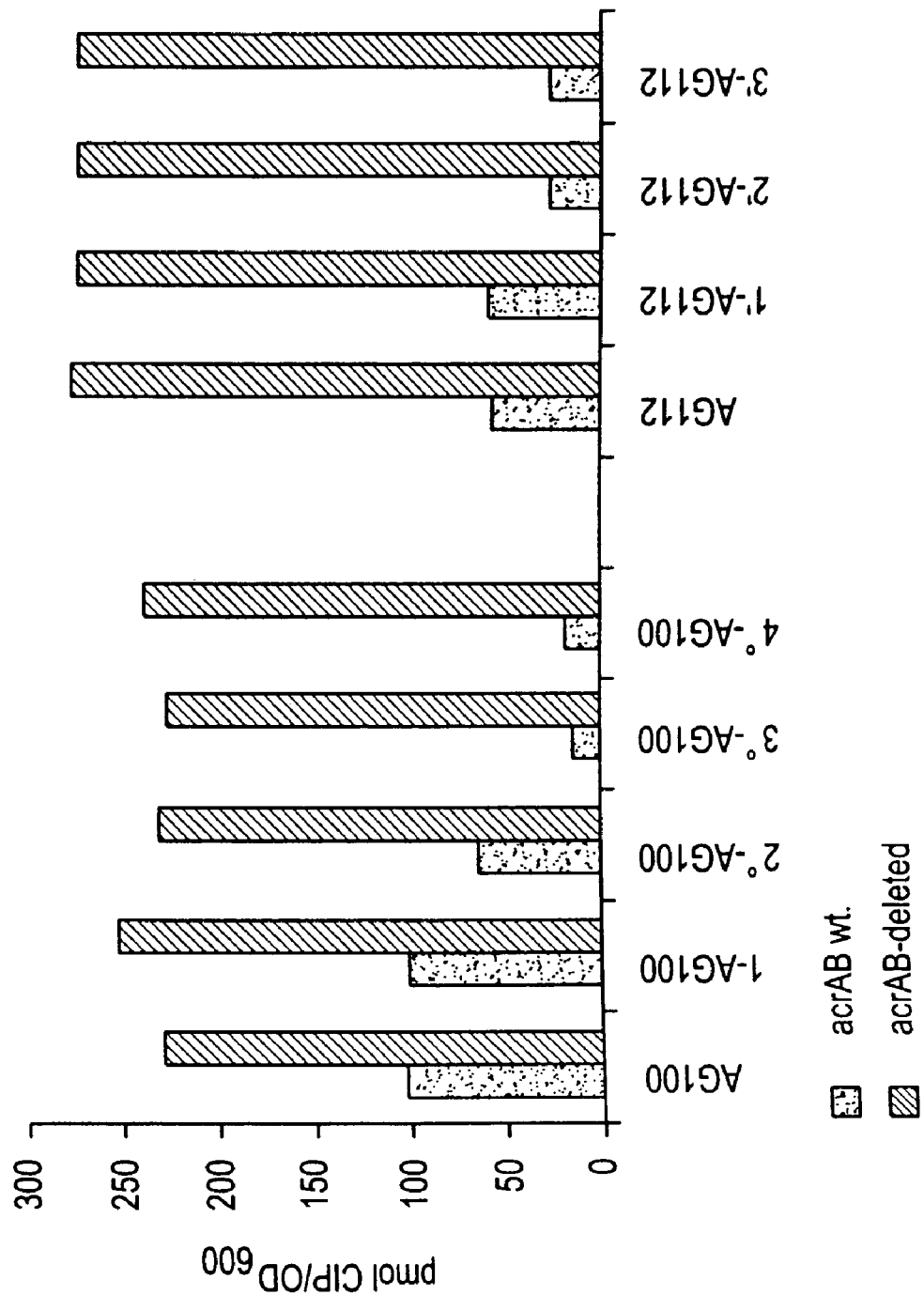
FIG. 1 shows accumulation of ciprofloxacin (CIP) by energized cells. [$^{14}$C-]ciprofloxacin uptake by fluoroquinolone-resistant mutants derived in vitro from E. coli-K12 strains AG100 and AG112 was assayed at 30° C. at equilibrium after addition of 10 µM ciprofloxacin. Cells carried either the wild-type acrAB gene (solid bars) or an acrAB-deletion (hashed bars).

The present invention represents an advance in controlling resistance to drugs which are substrates of AcrAB-like efflux pumps. In preferred embodiments, the methods of the invention can be used to control resistance to antibiotic agents and non-antibiotic agents. In a particularly preferred embodiment, drugs which are substrates of AcrAB-like efflux pumps include antibiotics, e.g., fluoroquinolones or rifampin. The invention further pertains to AcrAB-like efflux pump inhibitors obtained using the instant methods and their methods of use. In another particularly preferred embodiment, drugs include non-antibiotic agents, e.g., triclosan. The subject methods are effective in controlling drug resistance even among highly resistant microbes that bear chromosomal mutations which alter drug target molecules. For example, analysis of microbial mutants has revealed that mutations in the fluoroquinolone target gene gyrA, the regulatory gene marR, and additional, as yet unidentified genes probably affecting AcrAB-mediated efflux of ciprofloxacin all contributed to fluoroquinolone resistance. Surprisingly, inactivation of the AcrAB locus made even highly resistant cells hypersusceptible to fluoroquinolones and certain other unrelated drugs even among topoisomerase mutants. These studies indicate that blocking the function of AcrAB-like efflux pumps reduces even high-level drug resistance.

Accordingly, the invention provides, inter alia, methods of screening for compounds which reduce drug resistance, in particular to antibiotics and non-antibiotic agents such as fluoroquinolones and triclosan, and methods of screening for compounds that specifically block an AcrAB-like efflux pump. In addition, the invention provides methods of enhancing the antimicrobial activity of a drug and methods of treating infection.

Before further description of the invention, certain terms employed in the specification, examples and appended claims are, for convenience, collected here.

I. Definitions

As used herein the term "infection" includes the presence of a microbe in or on a subject which, if its growth were inhibited, would result in a benefit to the subject. As such, the term "infection" in addition to referring to the presence of pathogens also includes normal flora which is not desirable, e.g., on the skin of a burn patient or in the gastrointestinal tract of an immunocompromised patient. As used herein, the term "treating" refers to the administration of a compound to a subject, for prophylactic and/or therapeutic purposes. The term "administration" includes delivery to a subject, e.g., by any appropriate method which serves to deliver the drug to the site of the infection. Administration of the drug can be, e.g., oral, intravenous, or topical.

As used herein, the term "drug" includes compounds which are substrates of AcrAB-like efflux pumps. The term "drug" includes compounds which reduce the growth of a microbe e.g., which reduce the ability of a microbe to produce infection in a host, or which reduce the ability of a microbe to multiply or remain infective in the environment. Such drugs include antibiotic agents and non-antibiotic agents. The term "drug" includes antiinfective compounds which are static or cidal for microbes, e.g., an antimicrobial compound which inhibits the growth and/or viability of a microbe. Preferred antiinfective compounds increase the susceptibility of microbes to antibiotics or decrease the infectivity or virulence of a microbe. Substrates of the AcrAB-like efflux pumps can be readily identified using methods known in the art and described in further detail herein. For example, putative drugs which are substrates of AcrAB-like efflux pumps can be labeled, e.g., radioactively, and their export from a microbial cell tested in microbial cells which possess AcrAB-like efflux pumps and in microbial cells which lack AcrAB-like efflux pumps. Those agents which are present at a higher intracellular concentration in microbes that lack such pumps than in microbes that possess such pumps are drugs which are substrates of the pump.

The term "drug" includes the antimicrobial agents to which the Mar phenotype has been shown to mediate resistance and, as such, includes disinfectants, antiseptics, and surface delivered compounds. For example, antibiotics, biocides, or other type of antibacterial compounds, including agents which induce oxidative stress agents, and organic solvents are included in this term. The term "drug" also includes biocidal agents. The term "biocidal" is art recognized and includes an agent that those ordinarily skilled in the art prior to the present invention believed would kill a cell "non-specifically," or a broad spectrum agent whose mechanism of action is unknown, e.g., prior to the present invention, one of ordinary skill in the art would not have expected the agent to be target-specific. Examples of biocidal agents include paraben, chlorbutanol, phenol, alkylating agents such as ethylene oxide and formaldehyde, halides, mercurials and other heavy metals, detergents, acids, alkalis, and chlorhexidine. Other biocidal agents include: triclosan, pine oil, quaternary amine compounds such as alkyl dimethyl benzyl ammonium chloride, chloroxylol, chlorhexidine, cyclohexidine, triclocarbon, and disinfectants. The term "bactericidal" refers to an agent that can kill a bacterium; "bacteriostatic" refers to an agent that inhibits the growth of a bacterium.

The term "antibiotic" is art recognized and includes antimicrobial agents synthesized by an organism in nature and isolated from this natural source, and chemically synthesized drugs. The term includes but is not limited to: polyether ionophore such as monensin and nigericin; macrolide antibiotics such as erythromycin and tylosin; aminoglycoside antibiotics such as streptomycin and kanamycin; β-lactam antibiotics such as penicillin and cephalosporin; and polypeptide antibiotics such as subtilisin and neosporin. Semi-synthetic derivatives of antibiotics, and antibiotics produced by chemical methods are also encompassed by this term. Chemically-derived antimicrobial agents such as isoniazid, trimethoprim, quinolones, fluoroquinolones and sulfa drugs are considered antibacterial drugs, and the term antibiotic includes these. It is within the scope of the screens of the present invention to include compounds derived from natural products and compounds that are chemically synthesized.

In contrast to the term "biocidal," an antibiotic or an "anti-microbial drug approved for human use" is considered to have a specific molecular target in a microbial cell. Preferably a microbial target of a therapeutic agent is sufficiently different from its physiological counterpart in a subject in need of treatment that the antibiotic or drug has minimal adverse effects on the subject.

The phrase "non-antibiotic agent" includes substrates of an acrAB-like efflux pump which are not art recognized as being antibiotics. Exemplary non-antibiotic agents include, e.g., biocides, disinfectants or antiinfectives. Non antibiotic agents also include substrates of an acrAB-like efflux pump which are incorporated into consumer goods, e.g., for topical use on a subject or as cleaning products.

As used herein, the term "fluoroquinolone" includes quinolones substituted with at least one fluorine atom. Preferred fluoroquinolones include compounds with the carbonyl at the 4 position. Preferred positions for fluorine substitution include the 5, 6, and 7 positions. Derivatives include compounds with additional substituents such as, although not limited to, NR'R", CN, $NO_2$, F, Cl, Br, I, $CF_3$, $CCl_3$, $CHF_2$, $CHCl_2$, CONR'R", S(O)NR'R", CHO, $OCF_3$, $OCCl_3$, $SCF_3$, $SCCl_3$, COR', $CO_2R'$, and OR' and wherein R' and R" are each independently hydrogen, $C_1$–$C_4$ alkyl, $C_2$–$C_4$ alkenyl, $C_2$–$C_4$ alkynyl or optionally substituted cyclic or heterocyclic groups. The term fluoroquinolone also encompasses compounds with heterocyclic substitutions at the seven position, such as naphthyridinones. Preferred substituents include piperazinyl groups and other heterocyclic groups, carboxylic acid groups and substituted or unsubstituted alkyl groups. One example of a preferred fluoroquinolone is shown below, wherein X is CH or N or $CR_6$, and where $R_1$ is lower alkyl including cycloalkyl groups, or optionally substituted with halogens; $R_2$, $R_3$, and $R_4$ are each independently substituted or unsubstituted lower alkyl or hydrogen; $R_5$ is fluorine, hydrogen or amino; and $R_6$ is hydrogen or fluorine.

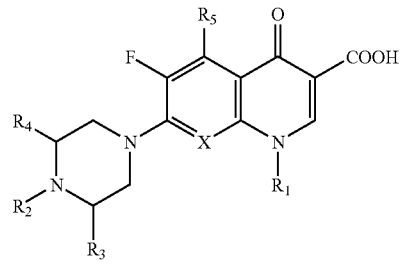

As used herein, the term "multiple drug resistance (MDR)" includes resistance to both antibiotic and non-antibiotic compounds. MDR results from the increased transcription of a chromosomal or plasmid encoded genetic locus in an organism, e.g., a marRAB locus, that results in the ability of the organism to minimize the toxic effects of a compound to which it has been exposed, as well as to other non-related compounds, e.g., by stimulating an efflux pump(s) or microbiological catabolic or metabolic processes. As used herein, the phrase "microbes which are resistant to drugs or drug resistant microbes" includes microbes that are characterized by a mutation in a target gene or by increased transcription of a genetic locus that affects drug resistance, e.g., an efflux pump gene.

As used herein, the phrase "microbes which are resistant to drugs or drug resistant microbes" includes microbes that are characterized by mutations in a gene that is the target of a drug.

As used herein, the phrase "microbes which are highly resistant to drugs or highly drug resistant microbes" includes microbes that are characterized by mutations in multiple (i.e., more than one) gene that affects drug resistance. Preferably, a microbe that is highly resistant to drugs is characterized by at least two of the following three traits: (1) it comprises at least one mutation in a gene encoding a drug target that renders the microbe resistant to one or more drugs (e.g., a gyrase, fabI or topoisomerase mutation); (2) it comprises a second mutation (to the same gene or a different gene than in (1)) that increases drug resistance; and (3) it has increased expression of at least one efflux pump (e.g., as a result of increased transcription of the mar locus). The term "mutation" includes an alteration (e.g., a substitution, deletion, or insertion) of at least one nucleotide in the sequence of a nucleic acid molecule (either chromosomal or episomal) in a microbe which is capable of influencing drug resistance. Such a mutation can result, e.g., in altered gene regulation in the microbe or in the expression of an altered polypeptide. Preferably, such mutations are in genes which encode the target of the drug to which the microbe is resistant.

In one embodiment, the drug is an antibiotic. In a preferred embodiment, the drug is a fluoroquinolone.

In another embodiment, the drug is a non-antibiotic agent, e.g., triclosan, pine oil, quaternary amine compounds such as alkyl dimethyl benzyl ammonium chloride, chloroxylol, triclocarbon, or a disinfectant, described in further detail herein. In a particularly preferred embodiment, the drug is a substrate of an acrAB-like efflux pump which is not a non-antibiotic agent.

Microbes that are highly resistant to drugs are more resistant to drugs than microbes that that are characterized by only one of the preceding traits. In general, antibiotics, when tested for their effect on the growth of such highly resistant microbes, will yield a minimal inhibitory concentration (MIC) from between about 2-fold to more than 100-fold higher than that observed for a microbe that is characterized by only one of the above traits or a microbe that is multiply antibiotic resistant, but not highly resistant to drugs.

As used herein the term "drug target" includes molecules which are acted on by drugs and which, in a non-resistant microbe, are altered such that they do not retain their normal function and the growth of the microbe is inhibited. For example, exemplary drug targets include: the DNA gyrase and topoisomerase molecules, which are targets of fluoroquinolone antibiotics; RNA polymerase, which is a target of rifampin; and FabI, which is a target of triclosan (Heath R J, e.t. al. 1999. *J Biol Chem*; 274; Levy C W et al. 1999. *Nature* 398: 383–4; McMurry L M; et al. 1998. *Nature*. 394: 531). In one embodiment, a drug target is not FabI.

As used herein the term "AcrAB-like efflux pump" includes efflux pumps that have homology with the AcrAB efflux pump of *E. coli*. The AcrAB pump is a resistance, nodulation, and division (RND)-type pump. RND pumps have 12 transmembrane helices. The acrA and acrB genes have been cloned and sequenced (Ma et al. 1993. *J. Bacteriol.* 175:6229). The sequences of AcrAB in *E. coli* are deposited as GenBank accession number U00734. The AcrAB genes have other homologs in *E. coli*, as well as homologs in other species of bacteria. For example, homologs of the AcrAB efflux pump have been identified in *Haemophilus influenzae*, (Sanchez et al. 1997. *J. Bacteriol.* 179:6855) and in *Salmonella typhimurium* (Nikaido et al. 1998. *J. Bacteriol.* 180:4686). Exemplary homologues of AcrAB include: MtrCD, MexAB-OprM, MexCD-OprJ, MexEF-OprN, and YhiUV. Such homologs can be readily identified by one of ordinary skill in the art based on shared homology and structure with the AcrAB pump and/or based on similarities in the compounds which they export. Isolation of novel AcrAB-like efflux pumps from other microbes can be carried out using techniques which are known in the art, e.g., nucleic acid hybridization and functional cloning.

As used herein the term "AcrAB-like efflux pump inhibitor" refers to a compound which interferes with the ability of an AcrAB-like efflux pump to export a compound which it is normally capable of exporting in the absence of such an inhibitor. Such inhibitors can inhibit the activity of an AcrAB-like efflux pump directly, e.g., by blocking the pump, or indirectly, e.g., by reducing transcription of acrA-like and/or acrB-like genes. Inhibitors of AcrAB-like efflux pumps can inhibit the growth of resistant and/or highly resistant microbes which used alone, or they may potentiate the activity of a drug to which the microbe is resistant.

As used herein the term "non-AcrAB-like efflux pump" includes efflux pumps which are not related to the AcrAB efflux pump of *E. coli*. Such pumps include, e.g., major facilitator pumps, membrane fusion proteins, and ABC (ATP-binding cassette) pumps.

As used herein the term "growth" in reference to the growth of a microbe includes the reproduction or population expansion of the microbe, e.g., increase in numbers rather than increase in size. The term also includes maintenance of on-going metabolic processes of a microbe, e.g., those processes that keep the cell alive when the cell is not dividing.

As used herein the term "reporter gene" includes any gene which encodes an easily detectable product which gene is operably linked to a promoter. By operably linked it is meant that under appropriate conditions an RNA polymerase may bind to the promoter of the regulatory region and proceed to transcribe the nucleotide sequence of the reporter gene. In preferred embodiments, a reporter gene construct consists of a promoter linked to a reporter gene. In certain embodiments, however, it may be desirable to include other sequences, e.g., transcriptional regulatory sequences, in the reporter gene construct. For example, modulation of the activity of the promoter may be affected by altering the RNA polymerase binding to the promoter region, or, alternatively, by interfering with initiation of transcription or elongation of the mRNA. Thus, sequences which are herein collectively referred to as transcriptional regulatory elements or sequences may also be included in the reporter gene construct. In addition, the construct may include sequences of nucleotides that alter translation of the resulting mRNA, thereby altering the amount of reporter gene product.

As used herein the term "test compound" includes reagents tested using the assays of the invention to determine whether they modulate an AcrAB-like efflux pump activity. More than one test compound, e.g., a plurality of test compounds, can be tested at the same time for their ability to modulate the activity of an AcrAB-like efflux pump in a screening assay.

Compounds that can be tested in the subject assays include antibiotic and non-antibiotic compounds. Exemplary test compounds which can be screened for activity include, but are not limited to, peptides, non-peptidic compounds, nucleic acids, carbohydrates, small organic molecules (e.g., polyketides), and natural product extract libraries. The term "non-peptidic compound" is intended to encompass compounds that are comprised, at least in part, of molecular structures different from naturally-occurring L-amino acid residues linked by natural peptide bonds. However, "non-peptidic compounds" are intended to include compounds composed, in whole or in part, of peptidomimetic structures, such as D-amino acids, non-naturally-occurring L-amino acids, modified peptide backbones and the like, as well as compounds that are composed, in whole or in part, of molecular structures unrelated to naturally-occurring L-amino acid residues linked by natural peptide bonds. "Non-peptidic compounds" also are intended to include natural products.

As used herein the phrase "indicator compound" includes compounds which are normally exported by an AcrAB-like efflux pump. Indicator compounds are used as markers of AcrAB-like efflux pump activity in order to determine the effect of a test compound on the activity of an AcrAB-like efflux pump. Exemplary indicator compounds include, e.g., antibiotics and dyes.

II. Inhibitors of AcrAB-Like Efflux Pumps

Known inhibitors of efflux pumps can be used in the methods and compositions of the invention. Exemplary inhibitors have been described previously in PCT published patent application WO96/33285 (including L-phenylalanyl-L-arginyl-β-naphthylamide). Methods for testing compounds for efflux pump inhibition are also described therein. Other useful inhibitors include ethanol (concentrations of about 4%), methanol, hexane and minocycline. Still other inhibitors include antisense nucleic acids and ribozymes directed against the gene(s) encoding the efflux pump. Characteristics of other efflux pump inhibitors are described, e.g., in WO 96/33285.

Other exemplary AcrAB-like efflux pump inhibitors include, e.g., antisense nucleic acids which bind to AcrAB genes and prevent transcription or translation thereof. Antibodies which bind efflux pumps or proteins which regulate the expression of efflux pumps are another class of inhibitors. Still other inhibitors include genes which repress expression of the efflux pumps or regulatory loci (such as marR) which regulate expression of efflux pumps. Increasing the amount of such genes or the expression products thereof can reduce the expression of efflux pumps in microbes.

As mentioned above, the invention embraces antisense nucleic acids, including oligonucleotides, that selectively bind to a nucleic acid molecule encoding an efflux pump (e.g. acrA) or a molecule which regulates expression of an efflux pump (e.g. marA, rob or soxS). As used herein, the term "antisense oligonucleotide" or "antisense molecule" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an RNA transcript of that gene and, thereby, inhibits the transcription of that gene and/or the translation of that RNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more strongly to the target sequence than to any other sequence in the target cell under physiological conditions. Based upon the nucleic acid sequence of a gene of interest, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or RNA transcripts, in preferred embodiments the antisense oligonucleotides correspond to N-terminal or 5' upstream sites such as translation initiation, transcription initiation or promoter sites. In addition, 3'-untranslated regions may be targeted. In addition, the antisense is targeted, preferably, to sites in which RNA secondary structure is not expected and at which proteins are not expected to bind.

In embodiment, the antisense oligonucleotides of the invention may be composed of "natural," i.e., unmodified deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by standard methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways as compared to naturally occurring oligonucleotides which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, provides preparations containing modified antisense molecules that are complementary to and can hybridize with, under physiological conditions, nucleic acids encoding mar/sox/rob or efflux pump polypeptides, together with one or more carriers.

As described above, the invention further embraces the use of antibodies or fragments of antibodies having the ability to selectively bind to efflux pumps, as well as polypeptides which regulate the expression of efflux pumps. The term "antibody" includes polyclonal and monoclonal antibodies, or fragments thereof, prepared according to conventional methodology.

Accordingly, in another embodiment, antibodies to AcrAB-like efflux pumps can be used as efflux pump inhibitors. Polyclonal anti-efflux pump antibodies can be prepared as described above by immunizing a suitable subject with an immunogen derived from an AcrAB-like efflux pump. The anti-efflux pump antibody titer in the immunized subject can be monitored over time by standard techniques, such as with an enzyme linked immunosorbent assay (ELISA) using immobilized efflux pump. If desired, the antibody molecules directed against efflux pump can be isolated from the mammal (e.g., from the blood) and further purified by well known techniques, such as protein A chromatography to obtain the IgG fraction. At an appropriate time after immunization, e.g., when the anti-efflux pump antibody titers are highest, antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol* 127:539–46; Brown et al. (1980) *J. Biol Chem* 255:4980–83; Yeh et al (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.*, 3:231–36). Briefly, an immortal cell line (typically a myeloma) is fused to lymphocytes (typically splenocytes) from a mammal immunized with a efflux pump immunogen as described above, and the culture supernatants of the resulting hybridoma cells are screened to identify a hybridoma producing a monoclonal antibody that binds specifically to an AcrAB-like efflux pump.

Any of the many well known protocols used for fusing lymphocytes and immortalized cell lines can be applied for the purpose of generating an anti-efflux pump monoclonal antibody (see, e.g., G. Galfre et al. (1977) *Nature* 266: 55052; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind efflux pump, e.g., using a standard ELISA assay.

As an alternative to preparing monoclonal antibody-secreting hybridomas, a monoclonal anti-efflux pump antibody can be identified and isolated by screening a recombinant combinatorial immunoglobulin library (e.g., an antibody phage display library) with efflux pump to thereby isolate immunoglobulin library members that bind efflux pumps. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J.* 12:725–734; Hawkins et al. (1992) *J Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348: 552–554.

Additionally, recombinant anti-efflux pump antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al International Patent Publication PCT/US86/02269; Akira, et al. European Patent Application 184,187; Taniguchi, M., European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

III. Methods of Screening for Novel Inhibitors

In one aspect, the invention provides a method for screening for an inhibitor of an AcrAB-like efflux pump. In this method, microbes expressing an AcrAB-like efflux pump are contacted with a test compound and a indicator compound. The test compound is a compound to be tested for its ability to inhibit an AcrAB-like efflux pump. An indicator compound is one which is normally exported by the AcrAB-like efflux pump. Using the subject methods the ability of a test compound to inhibit the activity of an AcrAB-like efflux pump is demonstrated by determining whether the intracellular concentration of the indicator compound (e.g., a fluoroquinolone or a dye) is elevated in the presence of the test compound. If the intracellular concentration of the indicator compound is increased in the presence of the test compound as compared to the intracellular concentration in the absence of the test compound, then the test compound can be identified as an inhibitor of an AcrAB-like efflux pump. Thus, one can determine whether or not the test compound is an inhibitor of an AcrAB-like efflux pump by showing that the test compound affects the ability of an AcrAB-like efflux pump present in the microbe to export the indicator compound.

The "intracellular concentration" of an indicator compound includes the concentration of the indicator compound inside the outermost membrane of the microbe. The outermost membrane of the microbe can be, e.g., a cytoplasmic membrane. In the case of Gram-negative bacteria, the relevant "intracellular concentration" is the concentration in the cellular space in which the indicator compound localizes, e.g., the cellular space which contains a target of the indicator compound.

Inhibitors identified using the subject methods can act directly on an AcrAB-like pump, e.g., by steric inhibition, or can act indirectly, e.g., influencing a more distal event, e.g., by modulating transcription of genes involved in the expression of the pump.

In one embodiment, the method comprises detecting the ability of the compound to reduce fluoroquinolone resistance in a microbe. For example, in one embodiment, the indicator compound comprises a fluoroquinolone and the effect of the test compound on the intracellular concentration of fluoroquinolone in the microbe is measured. In one embodiment, an increase in the intracellular concentration of fluoroquinolone can be measured directly, e.g., in an extract of microbial cells. For example, accumulation of a radiolabelled fluoroquinolone, e.g., [$^{14}$C-]ciprofloxacin can be determined using standard techniques. For instance, microbes can be contacted with a radiolabelled fluoroquinolone as an indicator composition in the presence and absence of a test compound. The concentration of the fluoroquinolone inside the cells can be measured at equilibrium by harvesting cells from the two groups (with and without test compound) and cell associated radioactivity measured with a liquid scintillation counter. In another embodiment, an increase in the intracellular concentration of fluoroquinolone can be measured indirectly, e.g., by a showing that a given concentration of fluoroquinolone when contacted with the microbe is sufficient to inhibit the growth of the microbe in the presence of the test compound, but not in the absence of the test compound.

In one embodiment of the subject assays, the step of determining whether the intracellular concentration of the indicator compound is elevated is accomplished by measuring a decrease in the minimal inhibitory concentration (MIC) of the indicator compound. Such an assay can be performed using a standard methods, e.g., an antibiotic disc assay.

In another embodiment, measurement of the intracellular concentration of an indicator compound can be facilitated by using an indicator compound which is readily detectable by spectroscopic means. Such a compound may be, for example, a dye, e.g., a basic dye, or a fluorophore. Exemplary indicator compounds include: acridine, ethidium bromode, gentian violet, malachite green, methylene blue, beenzyn viologen, bromothymol blue, toluidine blue, methylene blue, rose bengal, alcyan blue, ruthenium red, fast green, aniline blue, xylene cyanol, bromophenol blue, coomassie blue, bormocresol purple, bromocresol green, trypan blue, and phenol red.

In such an assay, the effect of the test compound on the ability of the cell to export the indicator compound can be measured spectroscopically. For example, the intracellular concentration of the dye or fluorophore can be determined indirectly, by determining the concentration of the indicator compound in the suspension medium or by determining the concentration of the indicator compound in the cells. This can be done, e.g., by extracting the indicator compound from the cells or by visual inspection of the cells themselves.

In another embodiment, the presence of an indicator compound in a microbe can be detected using a reporter gene which is sensitive to the presence of the indicator compound. Exemplary reporter genes are known in the art. For example, a reporter gene can provide a colorometric read out or an enzymatic read out of the presence of an indicator compound. In yet another embodiment, a reporter gene whose expression is inducible by the presence of a drug in a microbe can be used. For example, a microbe can be grown in the presence of a drug with and without a putative AcrAB-like efflux pump inhibitor. In cells in which the efflux pump is inhibited, the concentration of the drug will be increased and the reporter gene construct will be expressed. By this method, AcrAB-like efflux pump inhibitors are identified by their ability to inhibit the export rate of the drug and, thus, to induce reporter gene expression.

In another embodiment, a primary screening assay is used in which an indicator compound which does not comprise the drug of interest, e.g., a fluoroquinolone or triclosan is employed. In one embodiment, upon the identification of a test compound that increases the intracellular concentration of the test compound, a secondary screening assay is performed in which the effect of the same test compound on resistance to the drug of interest, e.g., fluoroquinolone resistance, is measured.

In another aspect, the invention provides a method of screening for compounds which specifically block an AcrAB-like efflux pump. In one embodiment the method involves contacting a microbe comprising an AcrAB-like efflux pump with a test compound and a indicator compound. The test compound is then tested for its ability to block an AcrAB-like efflux pump as described supra. The specificity of compounds which are identified as candidate AcrAB inhibitory agents can then be tested for their ability to block a non-AcrAB efflux pump. Compounds which block an AcrAB-like efflux pump and not a non-AcrAB efflux pump can be identified as compounds that specifically block an AcrAB-like efflux pump.

In one embodiment, the use of a compound which is identified as an inhibitor of an AcrAB-like efflux pump in the subject methods prevents the development of a drug resistant microbe or of a highly drug resistant microbe from a drug resistant microbe.

IV. Methods of Enhancing the Antimicrobial Activity of a Drug

In one aspect the invention pertains to methods of enhancing the antimicrobial activity of a drug by contacting a microbe that is resistant to one or more drugs with a drug to which the microbe is resistant and an inhibitor of an AcrAB-like efflux pump. In one embodiment, the microbe is contacted with the drug and the inhibitor of the AcrAB-like efflux pump ex vivo. This method can be used, e.g., in disinfecting surfaces to prevent the spread of infection or in cleaning surfaces which are fouled by microbial growth. Preferably, the drug used to contact the microbe is a non-antibiotic drug. In a preferred embodiment, the microbe is contacted with triclosan and an inhibitor of an AcrAB-like efflux pump.

In one embodiment, an AcrAB-like efflux pump inhibitor and a drug can be combined in a disinfectant, e.g., a cleaning product or a household product for contacting with resistant microbes. Exemplary cleaning products can be used topically on a subject (e.g., as soaps or lotions) or can be used for cleaning surfaces. In one embodiment, an AcrAB-like efflux pump inhibitor is itself a disinfectant.

V. Methods of Treating Microbial Infections

In one aspect the invention provides a method of treating a drug resistant infection in a subject comprising administering a drug to which a microbe is resistant and an inhibitor of an AcrAB-like efflux pump to the subject. As used herein the term "administration" includes contacting a drug with a subject, e.g. in vivo and/or in vitro. Thus, an efflux pump inhibitor and a drug can be administered for in vivo treatment or can be used topically, e.g., on skin or the eyes.

In one embodiment, the drug is an antibiotic, e.g., a fluoroquinolone. In another embodiment, the drug is a non-antibiotic composition, e.g., triclosan. In another embodiment the infection to be treated is one normally treated with a non-antibiotic composition. In another embodiment, the infection to be treated is not one normally treated with a non-antibiotic composition.

In one embodiment of the treatment method, the efflux pump inhibitor and the drug are administered separately to the subject. In another embodiment, the efflux pump inhibitor and the drug are administered simultaneously. In one embodiment, the simultaneous administration of the drug and the AcrAB-like efflux pump inhibitor is facilitated by the administration of a pharmaceutical composition comprising both an efflux pump inhibitor and a drug to which the microbe is resistant.

The amount of efflux pump inhibitor to be administered to a subject is a therapeutically effective amount, e.g., for an efflux pump inhibitor, an amount sufficient to reduce efflux pump activity. The dosage of efflux pump inhibitor to be administered to a subject that would benefit from treatment with a drug, e.g. a patient having an infection with a microbe, can readily be determined by one of ordinary skill in the art. Ideally, the dosage of efflux pump inhibitor administered will be sufficient to reduce efflux pump activity such that standard doses of drugs have a therapeutic effect, e.g., result in a benefit to the subject, e.g., by inhibiting microbial growth. The phrase "therapeutic effect" refers to an amelioration of symptoms or a prolongation of survival in a subject. In a preferred embodiment, a therapeutic effect is an elimination of a microbial infection.

In one embodiment, the subject is an avian subject, e.g., a chicken or a turkey. In another embodiment, the subject is a mammalian subject, e.g., a horse, sheep, pig, cow, dog, or cat. In a preferred embodiment, the subject is a human subject.

In one embodiment, an infection in a subject is treated prophylacticly. The term "prophylactic" treatment refers to treating a subject who is not yet infected, but who is susceptible to, or at risk of an infection. In one embodiment, the efflux pump inhibitor is administered prior to exposure to an infectious agent. In another embodiment, an efflux pump inhibitor is administered to a subject prior to the exposure of the subject to a drug resistant organism. The term "therapeutic" treatment refers to administering a compound to a subject already suffering from an infection.

In one embodiment an efflux pump inhibitor and/or drug may be administered in prodrug form, e.g., may be administered in a form which is modified within the cell to produce the functional form of the efflux pump inhibitor or fluoroquinolone.

Toxicity and therapeutic efficacy of such compounds can be determined by standard-pharmaceutical procedures in cell cultures or experimental animals, e.g., for determining the LD50 (the dose lethal for 50% of the population) and the ED50 (the does therapeutically effective in 50% of the population). The dose ratio between toxic and therapeutic effects is the therapeutic index and it can be expressed as the ratio between LD50/ED50. Compounds which exhibit large therapeutic indices are preferred. The data obtained from these cell culture assays and animal studies can be used in formulating a range of dosage for use in human subjects. The dosage of such compounds lies preferably within a range of circulating concentrations that include the ED50 with little or no toxicity. The dosage may vary within this range depending upon the dosage form employed and the route of administration utilized. For example, in one embodiment the therapeutic serum concentration of an efflux pump inhibitor is in the range of 0.1–100 ug/ml.

VI. Microbes

Numerous different microbes are suitable for use in testing for compounds that affect fluoroquinolone resistance or as sources of materials for use in the instant assays or as targets for growth inhibition. The term "microbe" includes any microorganism having a an AcrAB-like efflux pump. Preferably unicellular microbes including bacteria, fungi, or protozoa. In another embodiment, microbes suitable for use in the invention are multicellular, e.g., parasites or fungi. In preferred embodiments, microbes are pathogenic for humans, animals, or plants. As such, any of these disclosed microbes may be used as intact cells or as sources of materials for cell-free assays as described herein.

In preferred embodiments, microbes for use in the claimed methods are bacteria, either Gram-negative or Gram-positive bacteria. In a preferred embodiment, any bacteria that are shown to become resistant to antibiotics, e.g., to display MDR are appropriate for use in the claimed methods.

In preferred embodiments, microbes suitable for testing are bacteria from the family Enterobacteriaceae. In more preferred embodiments bacteria of a genus selected from the group consisting of: *Escherichia, Proteus, Salmonella, Klebsiella, Providencia, Enterobacter, Burkholderia, Pseudomonas, Acinetobacter, Aeromonas, Haemophilus, Yersinia, Neisseria*, and *Erwinia, Rhodopseudomonas*, or *Burkholderia* is used in the claimed assays.

In yet other embodiments, the microbes to be tested are Gram-positive bacteria and are from a genus selected from the group consisting of: *Lactobacillus, Azorhizobium, Streptococcus, Pediococcus, Photobacterium, Bacillus, Enterococcus, Staphylococcus, Clostridium, Butyrivibrio, Sphingomonas, Rhodococcus*, or *Streptomyces*

In yet other embodiments, the microbes to be tested are acid fast bacilli, e.g., from the genus *Mycobacterium*.

In still other embodiments, the microbes to be tested are, e.g., selected from a genus selected from the group consisting of: *Methanobacterium, Sulfolobus, Archaeoglobu, Rhodobacter*, or *Sinorhizobium*.

In other embodiments, the microbes to be tested are fungi. In a preferred embodiment the fungus is from the genus *Mucor* or *Candida*, e.g., *Mucor racemosus* or *Candida albicans*.

In yet other embodiments, the microbes to be tested are protozoa. In a preferred embodiment the microbe is a malaria or cryptosporidium parasite.

In one embodiment, the microbe is resistant to one or more drugs. In a preferred embodiment, the microbe is highly resistant to one or more drugs. In one embodiment, the drug is an antibiotic. In a preferred embodiment, the drug is a fluoroquinolone. In another embodiment, the drug is a non-antibiotic. In another embodiment, the drug is triclosan. In one embodiment, a microbe comprises a mutation in a gene which is a target of the drug to which the microbe is resistant, e.g., topoisomerase, gyrase, or fabI gene. In another embodiment, a microbe comprises a mutation in at least two of a topoisomerase, gyrase, or fabI gene.

VII. Test Compounds

Compounds for testing in the instant methods can be derived from a variety of different sources and can be known or can be novel. In one embodiment, libraries of compounds are tested in the instant methods to identify AcrAB-like efflux pump blocking agents. In another embodiment, known compounds are tested in the instant methods to identify AcrAB-like efflux pump blocking agents. In a preferred embodiment, compounds among the list of compounds generally regarded as safe (GRAS) by the Environmental Protection Agency are tested in the instant methods. In one embodiment, an AcrAB-like efflux pump inhibitor is itself a substrate of the pump.

A recent trend in medicinal chemistry includes the production of mixtures of compounds, referred to as libraries. While the use of libraries of peptides is well established in the art, new techniques have been developed which have allowed the production of mixtures of other compounds, such as benzodiazepines (Bunin et al. 1992. *J. Am. Chem. Soc.* 114:10987; DeWitt et al. 1993. *Proc. Natl. Acad. Sci. USA* 90:6909) peptoids (Zuckermann. 1994. *J. Med. Chem.* 37:2678) oligocarbamates (Cho et al. 1993. *Science.* 261: 1303), and hydantoins (DeWitt et al. supra). Rebek et al. have described an approach for the synthesis of molecular libraries of small organic molecules with a diversity of 104–105 (Carell et al. 1994. *Angew. Chem. Int. Ed. Engl.* 33:2059; Carell et al. *Angew. Chem. Int. Ed. Engl.* 1994. 33:2061).

The compounds for screening in the assays of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. *Anticancer Drug Des.* 1997. 12:145).

Exemplary compounds which can be screened for activity include, but are not limited to, peptides, nucleic acids, carbohydrates, small organic molecules (e.g., polyketides) (Cane et al. 1998. *Science* 282:63), and natural product extract libraries. In one embodiment, the test compound is a peptide or peptidomimetic. In another, preferred embodiment, the compounds are small, organic non-peptidic compounds.

Other exemplary methods for the synthesis of molecular libraries can be found in the art, for example in: Erb et al. 1994. *Proc. Natl. Acad. Sci. USA* 91:11422; Horwell et al. 1996 *Immunopharmacology* 33:68; and in Gallop et al. 1994. *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra). Other types of peptide libraries may also be expressed, see, for example, U.S. Pat. Nos. 5,270,181 and 5,292,646). In still another embodiment, combinatorial polypeptides can be produced from a cDNA library.

VIII. Pharmaceutical Compositions

The invention provides pharmaceutically acceptable compositions which include a therapeutically-effective amount or dose of an efflux pump inhibitor and one or more pharmaceutically acceptable carriers (additives) and/or diluents. A composition can also include a second antimicrobial agent, e.g., an antimicrobial compound, preferably an antibiotic, e.g., a fluoroquinolone.

As described in detail below, the pharmaceutical compositions can be formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream, foam, or suppository; or (5) aerosol, for example, as an aqueous aerosol, liposomal preparation or solid particles containing the compound.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the antimicrobial agents or compounds of the invention from one organ, or portion of the body, to another organ, or portion of the body without affecting its biological effect. Each carrier should be "acceptable" in the sense of being compatible with the other ingredients of the composition and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions. Proper fluidity can be maintained, for example, by the use of coating materials, such as lecithin, by the maintenance of the required particle size in the case of dispersions, and by the use of surfactants.

These compositions may also contain additional agents, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Pharmaceutical compositions of the present invention may be administered to epithelial surfaces of the body orally, parenterally, topically, rectally, nasally, intravaginally, intracisternally. They are of course given by forms suitable for each administration route. For example, they are administered in tablets or capsule form, by injection, inhalation, eye lotion, ointment, etc., administration by injection, infusion or inhalation; topical by lotion or ointment; and rectal or vaginal suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a sucrose octasulfate and/or an antibacterial or a contraceptive agent, drug or other material other than directly into the central nervous system, such that it enters the subject's system and, thus, is subject to metabolism and other like processes, for example, subcutaneous administration.

In some methods, the compositions of the invention can be topically administered to any epithelial surface. An "epithelial surface" according to this invention is defined as an area of tissue that covers external surfaces of a body, or which and lines hollow structures including, but not limited to, cutaneous and mucosal surfaces. Such epithelial surfaces include oral, pharyngeal, esophageal, pulmonary, ocular, aural, nasal, buccal, lingual, vaginal, cervical, genitourinary, alimentary, and anorectal surfaces.

Compositions can be formulated in a variety of conventional forms employed for topical administration. These include, for example, semi-solid and liquid dosage forms, such as liquid solutions or suspensions, suppositories, douches, enemas, gels, creams, emulsions, lotions, slurries, powders, sprays, lipsticks, foams, pastes, toothpastes, ointments, salves, balms, douches, drops, troches, chewing gums, lozenges, mouthwashes rinses.

Conventionally used carriers for topical applications include pectin, gelatin and derivatives thereof, polylactic acid or polyglycolic acid polymers or copolymers thereof, cellulose derivatives such as methyl cellulose, carboxymethyl cellulose, or oxidized cellulose, guar gum, acacia gum, karaya gum, tragacanth gum, bentonite, agar, carbomer, bladderwrack, ceratonia, dextran and derivatives thereof, ghatti gum, hectorite, ispaghula husk, polyvinypyrrolidone, silica and derivatives thereof, xanthan gum, kaolin, talc, starch and derivatives thereof, paraffin, water, vegetable and animal oils, polyethylene, polyethylene oxide, polyethylene glycol, polypropylene glycol, glycerol, ethanol, propanol, propylene glycol (glycols, alcohols), fixed oils, sodium, potassium, aluminum, magnesium or calcium salts (such as chloride, carbonate, bicarbonate, citrate, gluconate, lactate, acetate, gluceptate or tartrate).

Such compositions can be particularly useful, for example, for treatment or prevention of an unwanted cell, e.g., vaginal *Neisseria gonorrhea*, or infections of the oral cavity, including cold sores, infections of eye, the skin, or the lower intestinal tract. Standard composition strategies for topical agents can be applied to the antimicrobial compounds, or pharmaceutically acceptable salts thereof in order to enhance the persistence and residence time of the drug, and to improve the prophylactic efficacy achieved.

For topical application to be used in the lower intestinal tract or vaginally, a rectal suppository, a suitable enema, a gel, an ointment, a solution, a suspension or an insert can be used. Topical transdermal patches may also be used. Transdermal patches have the added advantage of providing controlled delivery of the compositions of the invention to the body. Such dosage forms can be made by dissolving or dispersing the agent in the proper medium.

Compositions of the invention can be administered in the form of suppositories for rectal or vaginal administration. These can be prepared by mixing the agent with a suitable non-irritating carrier which is solid at room temperature but liquid at rectal temperature and therefore will melt in the rectum or vagina to release the drug. Such materials include cocoa butter, beeswax, polyethylene glycols, a suppository wax or a salicylate, and which is solid at room temperature, but liquid at body temperature and, therefore, will melt in the rectum or vaginal cavity and release the active agent.

Compositions which are suitable for vaginal administration also include pessaries, tampons, creams, gels, pastes, foams, films, or spray compositions containing such carriers as are known in the art to be appropriate. The carrier employed in the sucrose octasulfate/contraceptive agent should be compatible with vaginal administration and/or coating of contraceptive devices. Combinations can be in solid, semi-solid and liquid dosage forms; such as diaphragm, jelly, douches, foams, films, ointments, creams, balms, gels, salves, pastes, slurries, vaginal suppositories, sexual lubricants, and coatings for devices, such as condoms, contraceptive sponges, cervical caps and diaphragms.

For ophthalmic applications, the pharmaceutical compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions can be formulated in an ointment such as petrolium. Exemplary ophthalmic compositions include eye ointments, powders, solutions and the like.

Powders and sprays can contain, in addition to sucrose octasulfate and/or antibiotic or contraceptive agent(s), carriers such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Compositions of the invention can also be orally administered in any orally-acceptable dosage form including, but not limited to, capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of sucrose octasulfate and/or antibiotic or contraceptive agent(s) as an active ingredient. A compound may also be administered as a bolus, electuary or paste. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Tablets, and other solid dosage forms, such as dragees, capsules, pills and granules, may be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the antimicrobial agent(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Sterile injectable forms of the compositions of this invention can be aqueous or oleaginous suspensions. These suspensions may be formulated according to techniques known in the art using suitable dispersing or wetting agents and suspending agents. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

In the case of AcrAB efflux pump inhibitors which are antisense nucleic acid molecules, the optimal course of administration of the oligomers may vary depending upon the desired result or on the subject to be treated. As used in this context "administration" refers to contacting cells with oligomers. The dosage of antisense molecule may be adjusted to optimally reduce expression of a protein translated from a target mRNA, e.g., as measured by a readout of RNA stability or by a therapeutic response, without undue experimentation. For example, expression of the protein encoded by the nucleic acid target can be measured to determine whether or dosage regimen needs to be adjusted accordingly. In addition, an increase or decrease in RNA and/or protein levels in a cell or produced by a cell can be measured using any art recognized technique. By determining whether transcription has been decreased, the effectiveness of the antisense molecule in inducing the cleavage of the target RNA can be determined.

As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Antisense molecule may be incorporated into liposomes or liposomes modified with polyethylene glycol or admixed with cationic lipids for parenteral administration. Incorporation of additional substances into the liposome, for example, antibodies reactive against membrane proteins found on specific target microbes, can help target the antisense molecule to specific cell types.

Moreover, the present invention provides for administering the subject oligomers with an osmotic pump providing continuous infusion of such antisense molecules, for example, as described in Rataiczak et at. (1992 Proc. Natl. Acad. Sci. USA 89:11823–11827). Such osmotic pumps are commercially available, e.g., from Alzet Inc. (Palo Alto, Calif.). Topical administration and parenteral administration in a cationic lipid carrier are preferred.

With respect to in vivo applications, the formulations of the present invention can be administered to a patient in a variety of forms adapted to the chosen route of administration, namely, parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation. Intravenous administration is preferred among the routes of parenteral administration.

Pharmaceutical preparations for parenteral administration include aqueous solutions of the active compounds in watersoluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran, optionally, the suspension may also contain stabilizers.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described antisense molecules may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the antisense molecule to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the antisense molecule at the lymph node. The antisense molecule can be modified to diffuse into the cell, or the liposome can directly participate in the delivery of either the unmodified or modified oligomer into the cell.

For prophylactic applications, the pharmaceutical composition of the invention can be applied prior to physical contact with a microbe. The timing of application prior to physical contact can be optimized to maximize the prophylactic effectiveness of the compound. The timing of application will vary depending on the mode of administration, the epithelial surface to which it is applied, the surface area, doses, the stability and effectiveness of composition under the pH of the epithelial surface, the frequency of application, e.g., single application or multiple applications. Preferably, the timing of application can be determined such that a single application of composition is sufficient. One skilled in the art will be able to determine the most appropriate time interval required to maximize prophylactic effectiveness of the compound.

One of ordinary skill in the art can determine and prescribe the effective amount of the pharmaceutical composition required. For example, one could start doses at levels lower than that required in order to achieve the desired therapeutic effect and gradually increase the dosage until the desired effect is achieved. In general, a suitable daily dose of a composition of the invention will be that amount of the composition which is the lowest dose effective to produce a therapeutic effect. Such an effective dose will generally depend upon the factors described above. It is preferred that administration be intravenous, intracoronary, intramuscular, intraperitoneal, or subcutaneous.

The practice of the present invention will employ, unless otherwise indicated, conventional techniques of cell biology, cell culture, molecular biology, genetics, microbiology, recombinant DNA, and immunology, which are within the skill of the art. Such techniques are explained fully in the literature. See, for example, *Genetics; Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, NY (1995)); *DNA Cloning*, Volumes I and II (D. N. Glover ed., 1985); *Oligonucleotide Synthesis* (M. J. Gait ed. (1984)); Mullis et al. U.S. Pat. No. 4,683,195; *Nucleic Acid Hybridization* (B. D. Hames & S. J. Higgins eds. (1984)); the treatise, *Methods In Enzymology* (Academic Press, Inc., N.Y); *Immunochemical Methods In Cell And Molecular Biology* (Mayer and Walker, eds., Academic Press, London (1987)); *Handbook Of Experimental Immunology*, Volumes I–IV (D. M. Weir and C. C. Blackwell, eds. (1986)); and Miller, J. *Experiments in Molecular Genetics* (Cold Spring Harbor Press, Cold Spring Harbor, N.Y. (1972)).

The contents of all references, pending patent applications and published patents, cited throughout this application are hereby expressly incorporated by reference.

The invention is further illustrated by the following examples, which should not be construed as further limiting.

EXAMPLES

Example 1

Preventing Efflux Via an AcrAB Pump Renders Highly Resistant Microbes Comprising Chromosomal Mutations in Drug Target Genes Sensitive to Drugs Ineffectiveness of Gyrase Mutations in *Escherichia coli* in the Absence of the AcrAB Multidrug Efflux Pump.

Fluoroquinolones [FQs] inhibit growth of wild-type *Escherichia coli* at very low concentrations. While FQ efflux is present in wild-type *E. coli* cells, its importance is minimal except when enhanced during the development of clinical resistance. To understand the role of the AcrAB efflux pump, which is under control of the mar and sox regulons, on the level of susceptibility and clinical resistance to FQs in *E. coli*, two series of *E coli* K-12 cells (derived from wild type AG100 and from the isogenic Mar mutant AG102) with FQ resistance were generated by amplification on ofloxacin [ofx]-containing plates in-vitro and mutations conferring resistance were characterized. P1-transduction was used to knock out AcrAB. Energy-dependent uptake of radiolabelled ciprofloxacin [cfx] into whole cells was measured in the presence and absence of AcrAB, and ofx MICs were determined by broth microdilution. In AG100, ofx resistance could be enhanced from 0.03 mg/l to 4 mg/l (128-fold) in four steps which included (in the order of occurrence): a gyrA mutation, a mar mutation, an undefined mutation, and a $2^{nd}$ gyrA mutation. AG102, starting out as a Mar mutant, was amplified in three steps from 0.125 mg/l to 8 mg/l (64-fold), which included one gyrA mutation and two as yet undefined mutations. Knock-out of AcrAB reduced the ofx MICs by factors of 4 through 128, producing a dramatic decrease in resistance mediated by topoisomerase mutations. Ofx MICs±AcrAB were as follows (in mg/l): AG100 series: 0.03/<0.015, 0.25/0.06, 1.0/0.06, 2.0/0.06, 4.0/0.125; AG102 series: 0.125/<0.015, 1.0/0.06, 4.0/0.06, 8.0/0.06. Active efflux of cfx was seen in the presence of the AcrAB efflux pump. Drug accumulation in energized, AcrAB-deleted mutants, however, was equivalent to that in de-energized cells, i.e., active efflux was completely abolished by deletion of AcrAB. Thus, the AcrAB multidrug efflux pump is the major, if not only, efflux pump in *E. coli* which controls the intracellular concentration of cfx. In its absence, high intracellular drug concentrations render topoisomerase mutations relatively ineffective in achieving clinical FQ resistance in *E. coli*.

Deletion of the AcrAB Efflux Pump Greatly Reduces Fluoroquinolone Resistance in Gyrase Mutants of *Escherichia coli*

Fluoroquinolone-resistant mutants were selected from a wild-type *Escherichia coli* K12 strain and its Mar mutant by stepwise exposure to increasing levels of ofloxacin on solid medium. Analysis of mutational steps by Northern (RNA) blot analysis, sequencing and accumulation studies with radiolabelled ciprofloxacin showed that mutations in the target gene gyrA, the regulatory gene marR and additional, as yet unidentified genes probably affecting AcrAB-mediated efflux of ciprofloxacin all contributed to fluoroquinolone resistance. Inactivation of the acrAB locus made all strains hypersusceptible to fluoroquinolones and certain other unrelated drugs. These studies indicate that wild-type function of the AcrAB efflux pump is required for expression of clinical fluoroquinolone resistance mediated by topoisomerase mutations.

Fluoroquinolone (FQ) resistance in *Escherichia coli* can be caused by mutations in the target proteins of the drugs, DNA gyrase (Hooper, D. C. et al., 1987. *The American Journal of Medicine* 82:12–20; Piddock, L. J. V. 1995. *Drugs* 49:29–35) and topoisomerase IV (Heisig, P. 1996. *Antimicrob. Agents Chemother.* 40:879–885). Mutations affecting regulatory genes such as marA (Cohen, S. P., et al. 1993. *J. Bacteriol.* 175: 1484–1492, Cohen, S. P., et al. 1989. *Antimicrob. Agents Chemother.* 33:1318–1325) or soxS (Amábile-Cuevas, C. F. and B. Demple. 1991. *Nucleic Acids Research* 19:4479–4484) also lead to resistance. The latter genes regulate intracellular drug concentrations, either by decreased uptake and/or increased efflux of the drug (Alekshun, M. N. and S. B. Levy. 1997. *Agents Chemother.* 41: 2067–2075). In *E. coli*, overexpression of MarA causes decreased expression of the OmpF porin (Cohen, S. P., et al. 1988. *J. Bacteriol.* 170:5416–5422) and increased AcrAB expression (Okusu, H., et al. 1996. *J. Bacteriol.* 178:306–308), thereby conferring resistance to a large number of antimicrobials (Alekshun, M. N. and S. B. Levy. 1997. *Antimicrob. Agents Chemother.* 41: 2067–2075)). The sequence of events leading to high-level, clinically significant FQ resistance is still poorly understood. Studies on clinical FQ-resistant strains are of limited help because one usually cannot isolate the parental strain. Studies with mutants selected in vitro have been limited to descriptions of phenotypic differences (MICs, outer membrane profiles, accumulation of fluoroquinolones) or focussed on mutations in the regions of gyrA and/or parC which determine quinolone resistance (QRDR) (Heisig, P. 1996. *Antimicrob. Agents Chemother.* 40:879–885; Piddock, L. J. V., et al. 1991. *J. Antimicrob. Chemother.* 28:185–198; Tenney, J. H., et al. 1983. *Antimicrob. Agents Chemother.* 23:188–189; Watanabe, M., et al. 1990. *Antimicrob. Agents Chemother.* 34:173–175). In this in vitro study the role of the AcrAB efflux pump was studied in FQ resistance mediated by topoisomerase mutations acquired during step-wise selection on ofloxacin. The AcrAB efflux pump was found to be critical to the FQ resistance level.

The following materials and methods were used in this example:

Antibiotics, chemicals and media. Ofloxacin (OFL) was kindly donated by Hoechst, Frankfurt, Germany. Radiolabelled [$^{14}$C-]ciprofloxacin was a generous gift of the Bayer AG, Leverkusen, Germany. Carbonyl cyanide m-chlorophenylhydrazone (CCCP) was purchased from Sigma Chemical Co., St. Louis, Mo., and organic solvents from Aldrich, Milwaukee, Wis. Strains were grown in LB broth (10 g of tryptone, 5 g of yeast extract and 10 g of NaCl per liter) unless otherwise noted.

Bacterial strains and plasmids. All strains were derivatives of plasmid-free *E. coli* K-12 strain AG100 (George, A. M. and S. B. Levy. 1983. *J. Bacteriol.* 155:531–540) and its Mar mutant AG112 which was selected on tetracycline in two steps (this study). Wild-type *E. coli* GC4468, its derived Sox mutant JTG1078 (soxR105; (Greenberg, J. T., et al. 1991. *J. Bact* 173:4433–4439)) and plasmid pSXS bearing the soxS gene on a 432 bp-fragment (Amábile-Cuevas, C. F. and B. Demple. 1991. *Nucleic Acids Research* 19:4479–4484). Strain JZM120 was as described (Ma, D., et al. 1995. *Mol Microbiol.* 16:45–55)

Selection of fluoroquinolone-resistant mutants. 1-AG100, 2°-AG100, 3*-AG100, 4*-AG100 and 1'-AG112, 2'-AG112, 3'-AG112 were sequential step mutants derived from AG100 and AG112, respectively, on solid media. For each step, about $10^{11}$ cells of an overnight culture were plated on several LB agar plates supplemented with increasing concentrations of OFL. Single colonies were further purified on OFL-supplemented agar plates. Mutant 2°-AG100 came out of one series, while mutants 3*- and 4*-AG100 came from a second series.

Susceptibility testing. MICs of selected antimicrobial agents were determined by a standard broth microdilution procedure with cation-adjusted Mueller-Hinton broth (Becton Dickinson, Cockeysville, Md.) and an inoculum of $5\times10^5$ CFU/ml according to NCCLS performance and interpretive guidelines (NCCLS. 1997. Methods for dilution antimicrobial susceptibility. Tests for bacteria that grow aerobically—Fourth Edition; Approved Standard. NCCLS document M7-A4 (ISBN 1-56238-309-4). NCCLS, 940 West Valley Road, Suite 1400, Wayne, Pa. 19087). Antimicrobial agents on the commercially available microtiter plates (Merlin Diagnostics GmbH, Bornheim, Germany) included the FQs ciprofloxacin (CIP), enoxacin, fleroxacin, nor-flo-xacin, ofloxacin (OFL), pefloxacin, sparfloxacin (SPX), and trovafloxacin (TVA). They also included tetracycline (TET), chloramphenicol (CML), trimethoprim (TMP), cefoxitin (CFOX), cefaclor, cefixim and loracarbef. MICs of bile salts were determined by a broth macrodilution procedure: sodium cholate and sodium deoxycholate were serially diluted twofold in LB broth and tubes inoculated at $5\times10^5$ CFU/ml. MICs of both antibiotics and bile salts were determined twice in independent experiments with reproducible results.

P1 transduction. AcrAB-deleted strains were constructed by P1 transduction (Provence, D. L. and R. Curtiss III. 1994. In: P. Gerhardt, R. G. E. Murray, W. A. Wood, and N. R. Krieg. (ed.), Methods for General and Molecular Bacteriology. American Society for Microbiology, Washington. pp. 317–347) of acrAB::Tn903kan$^r$ from strain JZM120 (Ma, D., et al. 1995. *Mol Microbiol.* 16:45–55) into AG100, AG112 and all derived FQ-resistant mutants. The AcrAB-deleted strains were designated AG100AK, 1-through 4*-AG100AK, AG112AK and 1'- through 3'-AG112AK. Two independent transductants were saved for each recipient. Deletion of AcrAB was confirmed by the absence of intact target DNA in a PCR assay and by greatly increased susceptibility to bile salts as previously reported (Thanassi, D. G., et al. 1997. *J. Bacteriol.* 179:2512–2518).

DNA sequencing. The QRDRs of gyrA (nucleotides 123 to 366) or parC (nucleotides 145 to 492) in the fluoroquinolone-resistant mutants were amplified by PCR and purified by use of Qia-quick spin columns (Qia-gen, Hilden, Germany), as previously described (Conrad, S., M. et al. 1996. *J. Antimicrob. Chemother.* 38:443–455, Conrad, S., et al. 1996. Program and Abstracts of the 36th Interscience Conference of Anti-microbial Agents and Chemotherapy, New Orleans. Abstract C9:35). marOR was amplified from bp 1311 to 1858 with primer pair ORAB2 and RK3 as described earlier (Oethinger, M., et al. 1998. *Agents Chemother.* 42:2089–2094). Direct cycle sequencing was performed in an automatic 373A DNA Sequencer (Applied Biosystems).

RNA extraction and Northern blot analysis. Northern blot analysis was performed as previously described in detail (Oethinger, M., et al 1998. *Antimicrob. Agents Chemother.* 42:2089–2094). In brief, RNA was harvested by a cesium chloride method from midlogarithmic phase cultures grown at 30° C. For assessment of the state of the marRAB operon or the soxRS operon, respectively, cultures were split and half the cultures induced with 5 mM sodium salicylate (marRAB operon) or 1.3 mM paraquat (soxRS operon), respectively. The level of transcription from both operons was assessed by hybridization of radiolabelled DNA probes (marA or soxS) to the membrane-bound RNA (20 μg/lane), exposure on a PhosphoImager screen, and visualization with ImageQuant Software (Molecular Dynamics, Sunnyvale, Calif.), as described recently (Oethinger, M., et al. 1998. *Antimicrob. Agents Chemother.* 42:2089–2094).

Accumulation of [$^{14}$C-]ciprofloxacin in whole cells. Cultures were grown to logarithmic phase in LB broth at 30° C., washed in 50 mM potassium phosphate/0.2% glucose (pH 7.4), and resuspended in the same buffer to $OD_{600}$=5–7. [$^{14}$C-]ciprofloxa-cin (specific activity: 59 mCi/mmol) was added to 10 μM. Accumulation was measured at equilibrium after 5 and 15 min by dilution of 50 μl of cell-labeling suspension into 5 ml of 100 mM LiCl/50 mM $KPO_4$ (pH 7.4), collection of cells immediately on Gelman metricel mixed-cellulose ester membrane filters (pore size, 0.45 μm; Gelman Sciences Inc., Ann Arbor, Mich.), and washing with 5 ml of the same buffer. Filters were dried, and radioactivity was assayed with a liquid scintillation counter, using Betafluor (National Diagnostics, Somerville, N.J.). Counting efficiency was 90%. Binding of radiolabel to filters in the absence of cells was subtracted. For conversion purposes, 10 μM CIP=3.15 μg/ml. When used, carbonyl cyanide m-chlorophenyl-hydrazone (CCCP), which destroys the proton motive force, was added to a final concentration of 200 μM, and accumulation of ciprofloxacin was assayed 5 and 15 min thereafter. The assay was designed in a way to investigate up to five strains in one experiment and to include, in addition, AG112 as a control strain. Results were calculated as accumulation of CIP in picomoles per $OD_{600}$ unit, where 1 $OD_{600}$ unit represented the number of cells in 1 ml when the $OD_{600}$ was equal to 1 (approximately $10^9$ E. coli cells, about 0.3 mg of protein). The ratio of CIP accumulation of de-energized cells divided by that of de-energized (CCCP-treated) cells was used as an indirect measure of active efflux (Levy, S. B. 1992. *Antimicrob. Agents Chemother.* 36:695–703). For these calculations, results obtained before (5 and 15 min) and after adding CCCP (25 min and 35 min) were averaged and ratios expressed as % of de-energized (i.e. maximum) accumulation.

The mutation frequencies of the different step mutants ranged between $8\times10^{-8}$ and $10^{-10}$ which agrees well with previous data (Heisig, P. 1996. *Antimicrob. Agents Chemother.* 40:879–885, Piddock, L. J. V., et al. 1991. *J. Antimicrob. Chemother.* 28:185–198, Watanabe, M., et al. 1990. Antimicrob. Agents Chemother. 34:173–175). None of the mutants was defective in growth. The first mutation step increased resistance to OFL by 8-fold in both AG100 and its Mar mutant AG112 (Table 1). Subsequent increases were 2- to 4-fold in all steps (Table 1 and Table 2) yielding the highest $MIC_{OFL}$ of 8 μg/ml in 3'-AG112. MICs of all FQs increased in parallel, with the order of MICs being: OFL>CIP>TVA=SPX (Table 2).

Identification of chromosomal mutations in structural and regulatory genes, and susceptibilities to unrelated antibiotics. Sequencing of the QRDRs of gyrA revealed that an identical point mutation at codon 87 (substitution of glycine for aspartate) occurred during the first mutation step in both AG100- and AG112-derived mutants (Table 1). These mutations led to an increase of MICs to FQs without an additional multiply resistance (Mar) phenotype. There are several reports about a gyrA mutation being the first "visible" mutation in the chain of events to higher FQ resistance during stepwise in vitro mutagenesis (Heisig, P. 1996. *Antimicrob. Agents Chemother.* 40:879–885, Kern, W. V., et al. 1997. Program and Abstracts of the 37th Interscience Conference of Antimicrobial Agents and Chemotherapy, Toronto (Abstract), Piddock, L. J. V., et al. 1991. *J. Antimicrob. Chemother.* 28:185–198). The concordance between AG100 and AG112 in the position of the first gyrA mutation may be coincidental.

The second step mutation in the AG100 background was a Mar mutation, as shown by overexpression of marRAB by Northern blot analysis of 2°-AG100. Such overexpression was found in three independently selected second step mutants of AG100. Constitutive overexpression of marA was associated with increased resistance to TET, CML and CFOX (Table 2). Retrospective sequencing of marOR showed that third step mutant 3*-AG 100 had not been derived from 2°-AG100 (Table 1). Despite many efforts, the putative second step Mar mutant 2*-AG100 with a 1643G→T transition in marOR could not be retrieved and further studied.

As expected (George, A. M. and S. B. Levy. 1983. *J. Bacteriol.* 155:531–540), marRAB was derepressed in Mar mutant AG112 and all subsequently derived mutants. Sequencing of marOR of the parental strain AG112 identified a 5 base pair deletion after the codon for amino acid 12, resulting in deletion of one amino acid and change of the complete protein sequence thereafter (Table 1). These data indicate that a single mutation in the gyrA gene confers a somewhat higher resistance than overexpression of marA by itself ($MIC_{OFL}$=0.25 μg/ml (8-fold) vs. 0.125 μg/ml (4-fold); 1-AG100 vs. AG112, Table 1) and that the two mutations are multiplicative ($MIC_{OFL}$=1 μg/ml (32-fold); 2°-AG100 and 1'-AG112, Table 1). During further steps to higher FQ resistance only one mutant, 4*-AG100, acquired a second mutation in gyrA at codon 83, substituting leucine for serine (Table 1). No additional mutations in gyrA, parC or marOR could be identified in any of the more resistant mutants, nor did they constitutively overexpress soxS at any step. Mutant 2'-AG112, derived from gyrA/Mar double mutant 1'-AG112, dis-played increased resistance to multiple drugs (Table 2) with no further mutation in marOR. The additional mutation possibly leads to upregulation of acrAB. In contrast, next step mutant 3'-AG112 had increased resistance to only FQs and CFOX (Table 2). The molecular basis for this resistance is also unknown.

Accumulation of CIP into whole energized cells reached a plateau by 5 min and averaged 103 pmol CIP/ODU$_{600}$ in AG100. When the proton motive force was dissipated by adding 200 µM CCCP, accumulation of [$^{14}$C-]ciprofloxacin doubled (201 pmol CIP/ODU$_{600}$). These findings confirmed earlier studies with norfloxacin (Cohen, S. P., et al. 1988. *Antimicrob. Agents Chemother.* 32:1187–1191) that FQ-susceptible *E. coli* cells use energy to reduce FQ accumulation, i.e. show active efflux. This phenomenon was also observed for *Proteus vulgaris* using ofloxacin (Ishii, H., et al. 1991. *J. Antimicrob. Chemother.* 28:827–836). In comparison, accumulation in AG112 was 54% of wild-type, averaging 56 pmol CIP/ODU$_{600}$, and increased to 226 pmol CIP/ODU$_{600}$ after CCCP. The rapid accumulation of CIP or norfloxacin (Cohen, S. P., et al. 1988. *Antimicrob. Agents Chemother.* 32:1187–1191) to the level of the AG100 parental strains upon deenergization of cells rules out downregulation of outer membrane porins as the major mechanism of reduced drug accumulation in Mar mutants. The amount of CIP accumulated by energized first step mutants 1-AG100 and 1'-AG112 and the increase in drug uptake following deenergization was virtually identical to that of parental strains AG100 and AG112, respectively. In second step Mar mutant 2°-AG100, accumulation decreased to 65 pmol CIP/ODU$_{600}$ (63% of wild-type; FIG. 1). Independently isolated mutants 3*- and 4*-AG100 showed even greater reduced accumulation (16 pmol CIP/ODU$_{600}$=, 16% of wild-type; and 20 pmol CIP/ODU$_{600}$, 19% of wild-type, respectively). Similarly, mutants 2'-AG112 and 3'-AG112 accumulated considerably less CIP than Mar mutants AG112 and 1'-AG112 (26 pmol CIP/ODU$_{600}$ for both strains vs. 56 pmol CIP/ODU$_{600}$ and 57 pmol CIP/ODU$_{600}$, respectively, or 25% vs. 54% and 55% of wild-type; FIG. 1). Due to more efficient efflux of the drug, the intracellular concentration of CIP in 3*-/4*-AG100 and 2'-/3'-AG112 at high external drug levels is likely similar to that of the parental strains at lower levels, so that the mutants can survive a higher extracellular FQ concentration. Whatever mechanism was underlying, it also increased the cells' resistance to TET, CML and CFOX.

Effects of deletion of acrAB. Upon deletion of the AcrAB multidrug efflux pump, active efflux of CIP was completely aborted in all strains; energized AG100 cells bearing the ΔacrAB deletion accumulated CIP to more than twice the level seen for energized acrAB$^+$ cells (FIG. 1). No difference in CIP uptake was noted between any strains bearing ΔacrAB irrespective of their mutations in marRAB or gyrA (FIG. 1). Although all ΔacrAB strains became profoundly hyper-susceptible to all FQs, mutants with newly acquired mutations in gyrA (Table 1) probably still retained the expected fold FQ resistance (Table 2). This resistance, however, was well below clinical significance. GyrA double mutant 4*-AG100ΔacrAB, for instance, displayed a MIC$_{OFL}$ of only 0.125 µg/ml. Interestingly, the differences in MICs for different FQs were no longer observed in ΔacrAB strains, e.g. in 2°-AG100 ΔacrAB$^+$, MIC$_{OFL}$=MIC$_{CIP}$=MIC$_{TVA}$= 0.06 µg/ml, while in the acrAB$^+$ strain 2°-AG100 MIC$_{OFL}$= 1 µg/ml, MIC$_{CIP}$=0.5 µg/ml, MIC$_{TVA}$=0.25 µg/ml (Table 2). For SPX MICs of all ΔacrAB mutants were below detection (MIC$_{SPX}$ Δ0.015 µg/ml). This may reflect a much higher proportion of drug being effluxed by the AcrAB pump in energized cells. Deletion of acrAB also eliminated the multidrug resistance conferred by overexpression of marA, thus underlining previous results that the AcrAB multidrug efflux pump plays a major role in the antibiotic resistance phenotype of Mar mutants (Okusu, H., D. Ma, and H. Nikaido. 1996. *J. Bacteriol.* 178:306–308). Effects of additional, as yet unknown mutations were also completely abolished by deletion of acrAB (Table 2). Thus, the effect of one or more additional mutation(s) on drug resistance may act via acrAB. Concluding Remarks. An earlier report on selection of norfloxacin-resistant *E. coli* noted no change of MICs of seven unrelated antibiotics during in vitro amplification of FQ-resistant mutants (Tenney, J. H., et al. 1983. *Antimicrob. Agents Chemother.* 23:188–189). Another study showed that only two out of ten second step mutants derived from a gyrA mutant displayed a multiply-resistant phenotype (Piddock, L. J. V., et al. 1991. *J. Antimicrob. Chemother.* 28:185–198).

The results of this study contrast with those previously reported: the stepwise sequence of mutational events during in vitro amplification of FQ resistance in three independent series involved an initial gyrA mutation followed by a mutation causing overexpression of the mar locus. A marOR mutation was also seen during the second mutation step during selection of FQ-resistant *E. coli* in vitro by others (Bagel, S., et al. 1999. *Antimicrob. Agents Chemother.* 43:868–875).

In recent experiments, identical in vitro experimental conditions were applied to select mutants of two clinical *E. coli* isolates (Kern, W. V., et al. 1997. Program and Abstracts of the 37th Interscience Conference of Antimicrobial Agents and Chemotherapy, Toronto (Abstract)). Since the second step mutant was a Mar mutant in one strain and a Sox mutant in the other (Kern, W. V., et al. 1997. Program and Abstracts of the 37th Interscience Conference of Antimicrobial Agents and Chemotherapy, Toronto (Abstract)), thus, a mutation in a regulatory gene occurs frequently. However, studies on FQ-resistant *E. coli* of clinical origin have shown that the proportion of constitutive Mar or Sox mutants is only between 10% and 15% (Oethinger, M., et al. 1998. Antimicrob. Agents Chemother. 42:2089–2094), a lower frequency than seen in the present in vitro experiments.

In view of the high number of pumps in *E. coli* (Nikaido, H. 1996. J. Bacteriol. 178:5853–5859, Paulsen, I. T., et al. 1996. Microbiol. Rev. 60:575–608) it is surprising that none of the other pumps actively effluxes CIP in the absence of AcrAB pump. Thus the AcrAB multidrug efflux pump appears to be the only or at least the most important pump which uses CIP as substrate.

These findings correspond with recent data on triclosan susceptibility of *E. coli* which was greatly affected by loss of the AcrAB pump (McMurry, L. M., et al. 1998. *FEMS Microbiol. Lett.* 166:305–309). While overexpression of acrAB, marA, or soxS increased the cells resistance to triclosan about two-fold, a mutation in the target of triclosan, enoyl reductase (encoded by fabI), rendered the cell about 100-fold more resistant (McMurry, L. M., et al. 1998. *Nature* 394:531–532). However, deletion of acrAB reduced the resistance 10-fold in all strains, rendering the fabI mutation less effective, similar to the decrease in effectiveness of topoisomerase mutations in the case of FQs.

The prominent finding of this work is that the AcrAB efflux pump has a powerful role in both the intrinsic and acquired level of resistance of *E. coli* to FQs. These data show that efflux mechanisms decrease the action of Fqs not only in *Pseudomonas* (Nikaido, H. 1996. *J. Bacteriol* 178: 5853–5859) but also in *E. coli*, even though in the latter organism the drugs diffuse rapidly through the more permeable porin channels (Nikaido, H. 1996. *J. Bacteriol.* 178: 5853–5859). Unidentified mutations in chromosomal loci in addition to marOR or soxRS modulate the level of resistance apparently by increasing efflux via AcrAB. Blockage of the AcrAB efflux pump would increase the potency of drugs such as FQs even in the face of topoisomerase mutations.

TABLE 1

Fluoroquinolone Resistance Mutations in *Escherichia coli* AG100 and its Mar mutant AG112

| Strain/Mutant | OFL MIC (μg/ml) | Fold Increase of OFL[a] MIC | Substitution in gyrA | Mutation In MarORAB | MarA Expression | CIP uptake (% of deenergized accumulation) |
|---|---|---|---|---|---|---|
| AG100 | 0.03 | — | — | — | wild-type | 51 |
| 1-AG100 | 0.25 | 8 | D87G | None | wild-type | 43 |
| 2°-AG100 | 1 | 32 | D87G | Asp67Tyr (1643G→T) | overexpression | 30 |
| 3*-AG100[b] | 2 | 64 | D87G | frameshift at aa12 (1485 + 1 bp) | overexpression | 9 |
| 4*-AG100[b] | 4 | 128 | S83L, D87G | frameshift at aa12 (1485 + 1 bp) | overexpression | 9 |
| AG112 | 0.125 | 4 | — | 5 bp deletion (Δ1481–1485) | overexpression | 25 |
| 1'-AG112 | 1 | 32 | D87G | 5 bp deletion (Δ1481–1485) | overexpression | 24 |
| 2'-AG112 | 4 | 128 | D87G | 5 bp deletion (Δ1481–1485) | overexpression | 12 |
| 3'-AG112 | 8 | 256 | D87G | 5 bp deletion (Δ1481–1485) | overexpression | 9 |

[a]Ofloxacin; Fold change in MIC as compared to AG100 (wild-type)
[b]Mutants designated with an * were not derived from 2°-AG100 in * mutants.

TABLE 2

Effects of deletion of acrAB on susceptibility of fluoroquinolone-resistant mutants of *Escherichia coli* AG100 and AG112

| | MIC[a] (μg/ml) | | | | | | | | | | | | | |
|---|---|---|---|---|---|---|---|---|---|---|---|---|---|---|
| | OFL[b] | | CIP[b] | | TVA[b] | | SPX[b] | | TET[b] | | CML[b] | | CFOX[b] | |
| Strain | acrAB+ | ΔacrAB | acrAB+ | ΔacrAB | acrAB+ | ΔacrAB | acrAB+ | ΔacrAB | acrAB+ | ΔacrAB | acrAB+ | ΔacrAB | acrAB+ | ΔacrAB |
| AG100 | 0.03 | ≤0.015 | ≤0.015 | ≤0.015 | 0.0625 | ≤0.03 | ≤0.015 | ≤0.015 | 1 | 0.5 | 4 | 1 | 4 | 0.5 |
| 1-AG100 | 0.25 | 0.06 | 0.25 | 0.06 | 0.25 | 0.06 | 0.125 | ≤0.015 | 2 | 1 | 4 | 1 | 4 | 0.5 |
| 2°-AG100 | 1 | 0.06 | 0.5 | 0.06 | 0.25 | 0.06 | 0.25 | ≤0.015 | 2 | 0.5 | 16 | 1 | 16 | 0.5 |
| 3*-AG100 | 2 | 0.06 | 1 | 0.06 | 0.5 | 0.06 | 0.5 | ≤0.015 | 8 | 1 | 32 | 1 | 32 | 0.5 |
| 4*-AG100 | 4 | 0.125 | 2 | 0.125 | 2 | 0.125 | 2 | ≤0.015 | 8 | 1 | 64 | 1 | 32 | 1 |
| AG112 | 0.125 | ≤0.015 | 0.06 | ≤0.015 | 0.125 | ≤0.03 | 0.06 | ≤0.015 | 4 | 1 | 16 | 1 | 32 | 1 |
| 1'-AG112 | 1 | 0.06 | 0.5 | 0.03 | 0.5 | 0.06 | 0.25 | ≤0.015 | 4 | 0.5 | 32 | 1 | 16 | 1 |
| 2'-AG112 | 4 | 0.06 | 2 | 0.03 | 1 | 0.06 | 1 | ≤0.015 | 16 | 1 | 64 | 1 | 32 | 0.5 |
| 3'-AG112 | 8 | 0.06 | 4 | 0.03 | 2 | 0.06 | 2 | ≤0.015 | 8 | 0.5 | 64 | 1 | 64 | 0.5 |

[a]Determined as broth microdilution according to NCCLS standards (#). Representative of experiments done in duplicate.
[b]OFL, ofloxacin; CIP, ciprofloxacin; TVA, trovafloxacin; SPX, sparfloxacin; TET, tetracycline; CML, chloramphenicol; CFOX, cefoxitin.

The contents of all references, pending patent applications and published patents, cited throughout this application are hereby expressly incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of screening for compounds which reduce antibiotic resistance in a highly antibiotic resistant microbe comprising an AcrAB or AcrAB-like efflux pump, wherein the microbe comprises at least two of the following traits: i) at least one chromosomal mutation in a gene encoding an antibiotic target that renders the microbe resistant to one or more antibiotics; ii) a second mutation, to the same gene or a different gene than in (i), that further increases antibiotic resistance, and iii) increased expression of at least one efflux pump, comprising: contacting the microbe with a test compound and measuring the effect of the test compound on the activity of the AcrAB or AcrAB-like efflux pump, wherein compounds which inhibit the activity of the AcrAB or AcrAB-like efflux pump are identified as compounds which reduce antibiotic resistance in the microbe.

2. The method of claim 1, wherein the microbe comprises all three of the traits.

3. The method of claim 1, wherein the microbe is highly resistant to fluoroquinolones.

4. The method of claim 1, wherein the at least one chromosomal mutation is present in a gene selected from the group consisting of: gyrase and topoisomerase.

5. The method of claim 1, wherein the microbe is a Gram negative bacterium.

6. The method of claim 1, wherein the microbe further comprises functional porin channels.

7. The method of claim 1, wherein the microbe is contacted with test compounds selected from a library of test compounds.

8. The method of claim 1, wherein the activity of the AcrAB or AcrAB-like efflux pump is determined by measuring efflux of an indicator compound which is a substrate of the efflux pump.

9. The method of claim 1, wherein the activity of the AcrAB or AcrAB-like efflux pump is determined by measuring growth of the microbe in an antibiotic.

10. The method of claim 1, wherein the efflux pump is AcrAB.

11. A method of screening for compounds which specifically inhibit the activity of an AcrAB or AcrAB-like efflux pump comprising:
   i) contacting a microbe comprising an AcrAB or AcrAB-like efflux and a non-AcrAB or non-AcrAB-like efflux pump and at least two of the following traits: i) at least one chromosomal mutation in a gene encoding a antibiotic target that renders the microbe resistant to one or more antibiotics; ii) a second mutation, to the same gene or a different gene than in (i), that further increases antibiotic resistance, and iii) increased expression of at least one efflux pump, with a test compound and an indicator compound;
   ii) testing the ability of the test compound to inhibit the activity of the AcrAB or AcrAB-like efflux pump;
   iii) testing the ability of the test compound to inhibit the activity of the non-AcrAB or non-AcrAB efflux pump;
   iv) and identifying compounds which inhibit the activity of the AcrAB or AcrAB-like efflux pump relative to the non-AcrAB or non-AcrAB-like efflux pump to thereby identify compounds which specifically inhibit the activity of the AcrAB or AcrAB-like efflux pump.

12. The method of claim 11, wherein the microbe is highly antibiotic resistant.

13. The method of claim 11, wherein the microbe is highly resistant to fluoroquinolones.

14. The method of claim 11, wherein the at least one mutation is present in a gene selected from the group consisting of: gyrase and topoisomerase.

15. The method of claim 11, wherein the microbe is a Gram negative bacterium.

16. The method of claim 11, wherein the microbe further comprises functional porin channels.

17. The method of claim 11, wherein the microbe is contacted with test compounds selected from a library of test compounds.

18. The method of claim 11, wherein the activity of the AcrAB or AcrAB-like efflux pump is determined by measuring efflux of an indicator compound which is a substrate of the efflux pump.

19. The method of claim 11, wherein growth of the microbe in an antibiotic is measured.

20. The method of claim 11, wherein the efflux pump is AcrAB.

21. A method of treating an infection in a subject caused by a microbe comprising an AcrAB or AcrAB-like efflux pump and at least two of the following traits: i) at least one chromosomal mutation in a gene encoding a antibiotic target that renders the microbe resistant to one or more antibiotics; ii) a second mutation, to the same gene or a different gene than in (i), that further increases antibiotic resistance, and iii) increased expression of at least one efflux pump, comprising: contacting the microbe with an antibiotic to which the microbe is resistant and an inhibitor of an acrAB or acrAB-like efflux pump such that the infection in the subject is treated.

22. The method of claim 21, wherein the subject is treated prophylactically.

23. The method of claim 21, wherein the subject is treated therapeutically.

24. The method of claim 21, wherein the microbe is highly resistant to fluoroquinolones.

25. The method of claim 21, wherein the at least one mutation is present in a gene selected from the group consisting of: gyrase and topoisomerase.

26. The method of claim 21, wherein the microbe is a Gram negative bacterium.

27. The method of claim 21, wherein the microbe further comprises functional porin channels.

* * * * *